(12) United States Patent
Zapol et al.

(10) Patent No.: US 11,497,878 B2
(45) Date of Patent: Nov. 15, 2022

(54) SYSTEMS AND METHODS FOR SYNTHESIS OF NITRIC OXIDE

(71) Applicant: The General Hospital Corporation, Boston, MA (US)

(72) Inventors: Warren Zapol, Cambridge, MA (US); Binglan Yu, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/520,137

(22) PCT Filed: Oct. 20, 2015

(86) PCT No.: PCT/US2015/056443
§ 371 (c)(1),
(2) Date: Apr. 19, 2017

(87) PCT Pub. No.: WO2016/064863
PCT Pub. Date: Apr. 28, 2016

(65) Prior Publication Data
US 2018/0296790 A1    Oct. 18, 2018

Related U.S. Application Data

(60) Provisional application No. 62/077,806, filed on Nov. 10, 2014, provisional application No. 62/065,825, filed on Oct. 20, 2014.

(51) Int. Cl.
*A61M 16/12* (2006.01)
*A61M 16/00* (2006.01)
(Continued)

(52) U.S. Cl.
CPC .......... *A61M 16/12* (2013.01); *A61M 16/009* (2013.01); *A61M 16/107* (2014.02);
(Continued)

(58) Field of Classification Search
CPC .. A61M 16/12; A61M 16/107; A61M 16/009; A61M 16/0051; A61M 16/022;
(Continued)

(56) References Cited

U.S. PATENT DOCUMENTS 2,485,481 A    10/1949    Cotton
2,525,938 A    10/1950    Peck
(Continued)

FOREIGN PATENT DOCUMENTS

CN    1099997 A    3/1995
CN    1730115 A    2/2006
(Continued)

OTHER PUBLICATIONS

International Search Report and Written Opinion for International Application No. PCT/US15/56443 dated Jan. 6, 2016.
(Continued)

*Primary Examiner* — Margaret M Luarca
(74) *Attorney, Agent, or Firm* — Quarles & Brady LLP

(57) ABSTRACT

Systems and methods for producing nitric oxide (NO) to be used in medical applications are provided. In some embodiments, systems and methods are provided for a NO generator that is capable of generating a desired concentration of NO to be provided to a respiratory system for inhalation by a patient.

45 Claims, 22 Drawing Sheets

(51) Int. Cl.
*A61M 16/10* (2006.01)
*C01B 21/32* (2006.01)
*C01B 21/30* (2006.01)

(52) U.S. Cl.
CPC ......... *A61M 16/1055* (2013.01); *C01B 21/30* (2013.01); *C01B 21/32* (2013.01); *A61M 2016/0039* (2013.01); *A61M 2016/1025* (2013.01); *A61M 2016/1035* (2013.01); *A61M 2202/0275* (2013.01)

(58) Field of Classification Search
CPC .............. A61M 16/024; A61M 16/104; A61M 2202/0275; C01B 21/32; B01J 19/088
See application file for complete search history.

(56) References Cited

U.S. PATENT DOCUMENTS

| | | | |
|---|---|---|---|
| 2,684,448 A | 7/1954 | Nilles, Jr. | |
| 3,047,370 A | 7/1962 | Avtges et al. | |
| 3,225,309 A | 12/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,680,694 A | 7/1987 | Huynh et al. | |
| 4,695,358 A | 9/1987 | Mizuno et al. | |
| 4,705,670 A | 11/1987 | O'Hare | |
| 4,816,229 A | 3/1989 | Jensen et al. | |
| 4,877,589 A | 10/1989 | O'Hare | |
| 5,285,372 A | 2/1994 | Huynh et al. | |
| 5,378,436 A | 1/1995 | Endoh et al. | |
| 5,396,882 A | 3/1995 | Zapol | |
| 5,413,097 A * | 5/1995 | Birenheide ............... A62B 7/10 128/202.22 | |
| 5,471,977 A | 12/1995 | Olsson et al. | |
| 5,485,827 A | 1/1996 | Zapol et al. | |
| 5,546,935 A | 8/1996 | Champeau | |
| 5,558,083 A | 9/1996 | Bathe et al. | |
| 5,573,733 A | 11/1996 | Salama | |
| 5,692,495 A * | 12/1997 | Sheu ..................... A61M 16/12 128/203.12 | |
| 5,732,693 A | 3/1998 | Bathe et al. | |
| 5,752,504 A | 5/1998 | Bathe | |
| 5,839,433 A | 11/1998 | Higenbottam | |
| 5,845,633 A | 12/1998 | Psaros | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,224,653 B1 | 5/2001 | Shvedchikov et al. | |
| 6,250,302 B1 | 6/2001 | Rantala | |
| 6,290,683 B1 | 9/2001 | Erez et al. | |
| 6,296,827 B1 | 10/2001 | Castor et al. | |
| 6,536,429 B1 | 3/2003 | Pavlov et al. | |
| 6,581,599 B1 | 6/2003 | Stenzler | |
| 6,668,828 B1 | 12/2003 | Figley et al. | |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,299,785 B1 | 11/2007 | Lee | |
| 7,312,584 B2 | 12/2007 | Tamita et al. | |
| 7,335,181 B2 | 2/2008 | Miller et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,520,866 B2 | 4/2009 | Stenzler et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,744,812 B2 | 6/2010 | Witherspoon et al. | |
| 7,861,717 B1 | 1/2011 | Krebs | |
| 7,955,294 B2 | 6/2011 | Stenzler et al. | |
| 8,030,849 B2 | 10/2011 | Suslov | |
| 8,043,252 B2 | 10/2011 | Miller et al. | |
| 8,079,998 B2 | 12/2011 | Hole et al. | |
| 8,151,791 B2 | 4/2012 | Arlow et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,344,627 B1 | 1/2013 | Hooke et al. | |
| 8,431,163 B2 | 4/2013 | Baldassarre et al. | |
| 8,518,457 B2 | 8/2013 | Miller et al. | |
| 8,573,209 B2 | 11/2013 | Bathe et al. | |
| 8,573,210 B2 | 11/2013 | Bathe et al. | |
| 8,574,531 B2 | 11/2013 | Miller et al. | |
| 8,717,733 B2 | 5/2014 | Gefter et al. | |
| 8,776,794 B2 | 7/2014 | Bathe et al. | |
| 8,776,795 B2 | 7/2014 | Bathe et al. | |
| 8,790,715 B2 | 7/2014 | Montgomery et al. | |
| 8,795,222 B2 | 8/2014 | Stenzler et al. | |
| 8,795,741 B2 | 8/2014 | Baldassarre | |
| 8,821,828 B2 | 9/2014 | Hilbig et al. | |
| 8,846,112 B2 | 9/2014 | Baldassarre | |
| 9,067,788 B1 | 6/2015 | Spielman et al. | |
| 9,095,534 B2 | 8/2015 | Stenzler et al. | |
| 9,265,911 B2 | 2/2016 | Bathe et al. | |
| 9,279,794 B2 | 3/2016 | Tolmie et al. | |
| 9,295,802 B2 | 3/2016 | Bathe et al. | |
| 9,408,993 B2 | 8/2016 | Bathe et al. | |
| 9,573,110 B2 | 2/2017 | Montgomery et al. | |
| 9,770,570 B2 | 9/2017 | Schnitman et al. | |
| 9,795,756 B2 | 10/2017 | Flanagan et al. | |
| 9,982,354 B2 * | 5/2018 | Kim ..................... B01J 19/088 | |
| 2001/0031230 A1 | 10/2001 | Castor et al. | |
| 2001/0037810 A1 * | 11/2001 | Fine ...................... A61K 33/00 128/203.26 | |
| 2004/0019274 A1 | 1/2004 | Galloway, Jr. et al. | |
| 2004/0028753 A1 | 2/2004 | Hedenstierna et al. | |
| 2004/0031248 A1 | 2/2004 | Lindsey | |
| 2004/0181149 A1 | 9/2004 | Langlotz et al. | |
| 2005/0108813 A1 | 5/2005 | Plut | |
| 2005/0172971 A1 | 8/2005 | Kolobow et al. | |
| 2005/0218007 A1 | 10/2005 | Pekshev et al. | |
| 2005/0263150 A1 | 12/2005 | Chathampally et al. | |
| 2005/0281465 A1 | 12/2005 | Marquart et al. | |
| 2006/0025700 A1 | 2/2006 | Fallik | |
| 2006/0172018 A1 | 8/2006 | Fine et al. | |
| 2006/0173396 A1 | 8/2006 | Hatamian et al. | |
| 2006/0276844 A1 | 12/2006 | Alon et al. | |
| 2007/0151561 A1 * | 7/2007 | Laurila ................. A61M 16/22 128/203.13 | |
| 2007/0190184 A1 | 8/2007 | Montgomery et al. | |
| 2008/0017030 A1 | 1/2008 | Fleck | |
| 2008/0078382 A1 * | 4/2008 | LeMahieu ........... A61M 16/107 128/200.24 | |
| 2008/0135044 A1 | 6/2008 | Freitag et al. | |
| 2008/0202509 A1 | 8/2008 | Dillon et al. | |
| 2010/0108493 A1 | 5/2010 | Wada et al. | |
| 2010/0122705 A1 | 5/2010 | Moenning, Jr. | |
| 2010/0189808 A1 | 7/2010 | Gupta et al. | |
| 2010/0245097 A1 | 9/2010 | Sung | |
| 2010/0275911 A1 | 11/2010 | Arlow et al. | |
| 2012/0037160 A1 | 2/2012 | Sung | |
| 2012/0258034 A1 * | 10/2012 | Hilbig .................... A61K 33/00 423/405 | |
| 2012/0279500 A1 | 11/2012 | Singvogel et al. | |
| 2012/0296265 A1 | 11/2012 | Dobrynin et al. | |
| 2013/0123801 A1 | 5/2013 | Umasuthan et al. | |
| 2013/0150863 A1 | 6/2013 | Baumgartner | |
| 2014/0031668 A1 | 1/2014 | Mobasser et al. | |
| 2014/0158121 A1 | 6/2014 | Flanagan et al. | |
| 2014/0216452 A1 * | 8/2014 | Miller .................. A61K 9/0073 128/202.26 | |
| 2014/0251787 A1 | 9/2014 | Montgomery et al. | |
| 2014/0363525 A1 | 12/2014 | Montgomery et al. | |
| 2015/0000659 A1 | 1/2015 | Martin | |

(56) References Cited

U.S. PATENT DOCUMENTS

| | | |
|---|---|---|
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0090261 A1 | 4/2015 | Crosbie |
| 2015/0174158 A1 | 6/2015 | Av-Gay et al. |
| 2015/0272988 A1 | 10/2015 | Av-Gay et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0183841 A1 | 6/2016 | Duindam et al. |
| 2016/0228670 A1 | 8/2016 | Av-Gay et al. |
| 2016/0243328 A1 | 8/2016 | Tolmie et al. |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0143758 A1 | 5/2017 | Greenberg et al. |
| 2017/0239289 A1 | 8/2017 | Av-Gay et al. |
| 2018/0125883 A1 | 5/2018 | Av-Gay et al. |
| 2018/0133246 A1 | 5/2018 | Av-Gay et al. |

FOREIGN PATENT DOCUMENTS

| | | |
|---|---|---|
| CN | 101828432 A | 9/2010 |
| EP | 0621051 A2 | 10/1994 |
| EP | 0763500 A2 | 3/1997 |
| EP | 1036758 A1 | 9/2000 |
| EP | 1854494 A1 | 11/2007 |
| EP | 2151554 A1 | 2/2010 |
| GB | 2277689 A | 11/1994 |
| JP | H04132560 A | 5/1992 |
| JP | 2000102616 A | 4/2000 |
| JP | 2001517108 A | 10/2001 |
| JP | 2004065636 A | 3/2004 |
| JP | 2006273677 A | 10/2006 |
| JP | 2014179563 A | 9/2014 |
| RU | 2199167 C1 | 2/2003 |
| WO | 9507610 A1 | 3/1995 |
| WO | 2004032719 A2 | 4/2004 |
| WO | 2008112143 A1 | 9/2008 |
| WO | 2011002606 A1 | 1/2011 |
| WO | 2012094008 A1 | 7/2012 |
| WO | 2012155213 A1 | 11/2012 |
| WO | 2013052548 A2 | 4/2013 |
| WO | 2013070712 A1 | 5/2013 |
| WO | WO 2013/181179 A1 | 12/2013 |
| WO | WO 2014/085719 A1 | 6/2014 |
| WO | WO 2014/143842 A1 | 9/2014 |
| WO | WO 2014/144151 A1 | 9/2014 |
| WO | 2015066278 A1 | 5/2015 |
| WO | 2015127085 A1 | 8/2015 |

OTHER PUBLICATIONS

Mok, et al., Application of Positive Pulsed Corona Discharge to Removal of SO2 and NOx, Proceedings, ICESP VII, Sep. 20-25, 1998, Kyongju, Korea, 8 pages.

Keshav, Using Plasmas for High-Speed Flow Control and Combustion Control, Dissertation for Degree of Doctor of Philosophy, The Ohio State University, 2008, 268 pages.

Namihira, et al., Production of Nitric Oxide Using a Pulsed Arc Discharge, IEEE Transactions on Plasma Science, 2002, 30(5):1993-1998.

PCT International Search Report, PCT/US2014/028439, dated Jul. 24, 2014.

PCT International Preliminary Report on Patentability, PCT/US2014/028439, dated Sep. 15, 2015.

PCT International Search Report, PCT/US2014/027986, dated Jul. 17, 2014.

PCT International Preliminary Report on Patentability, PCT/US2014/027986, dated Sep. 15, 2015.

Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages [Includes English Language Translation of Title Page and Abstract].

Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages [Includes English Language Translation of Title Page and Abstract].

Kuo, Air Plasma for Medical Applications, Journal of Biomedical Science and Engineering, 2012, 5:481-495.

Namihira et al., Production of Nitric Monoxide Using Pulsed Discharges for a Medical Application, IEEE Transactions on Plasma Science, 2000, 28(1):109-114.

Gao et al., Natural Convection at Microelectrodes, Analytical Chemistry, 1995, 67(9):1541-1545.

Encylopaedia Britannica, Inc., Definition of "Soda Lime", https://www.britannica.com/science/soda-lime, Nov. 12, 2018, 1 page.

Hui et al., The Effect of Flow Distribution on the Concentration of NO Produced by Pulsed Arc Discharge, Plasma Science and Technology, 2007, 9(6):766-769.

Intersurgical Complete Respiratory Systems, Carbon Dioxide Absorbents, Information Sheet, Issue 2 03.13, 8 pages.

Lorente, Chapter 20, Respiratory Filters and Ventilator-Associated Pneumonia: Composition, Efficacy Tests and Advantages and Disadvantages, In Humidification in the Intensive Care Unit, A.M. Esquinas (ed.), Springer-Verlag Berlin Heidelberg, 2012, pp. 171-177.

Hanning et al., Fortnightly Review—Pulse Oximetry: A Practical Review, BMJ, 1995, 311:367-370.

\* cited by examiner

SYSTEMS AND METHODS FOR SYNTHESIS OF NITRIC OXIDE

CROSS-REFERENCES TO RELATED APPLICATIONS

The present application represents the U.S. National Stage of International Application No. PCT/US2015/056443, filed Oct. 20, 2015 which is based on, claims priority to, and incorporates herein by reference in their entirety, U.S. Provisional Patent Application No. 62/065,825, filed Oct. 20, 2014, and entitled "Producing Nitric Oxide for Inhalation by Electric Discharge in Air," and U.S. Provisional Patent Application No. 62/077,806, filed Nov. 10, 2014, and entitled "Synthesis of Nitric Oxide."

STATEMENT REGARDING FEDERALLY SPONSORED RESEARCH

Not Applicable.

BACKGROUND

The disclosure relates generally to the electrical plasma synthesis of nitric oxide (NO) from gases and, more specifically, to systems and methods for producing safe NO to be used in medical applications.

NO is a crucial mediator of many biological systems, and is known to control the level of systemic and pulmonary artery blood pressure, help the immune system kill invading parasites that enter cells, inhibit the division of cancer calls, transmit signals between brain cells, and contribute to the death of brain cells that debilitates people with strokes or heart attacks, among other things. NO mediates the relaxation of smooth muscle present, for example, in the walls of blood vessels, bronchi, the gastrointestinal tract, and urogenital tract. Administration of NO gas to the lung by inhalation has been shown to produce localized smooth muscle relaxation within the lung's blood vessels and is widely used to treat pulmonary hypertension, pneumonia, hypoxemic respiratory failure of a newborn, etc. without producing systemic side effects.

Inhaling NO can immediately produce potent and selective pulmonary vasodilation that improves the matching of ventilation with perfusion, thereby increasing an injured lung's oxygen transport efficiency, and breathing NO can raise the arterial oxygen tension. Breathing NO produces the rapid onset of pulmonary vasodilator action occurring within seconds of commencing breathing with the absence of systemic vasodilatation. Once inhaled, NO diffuses through the pulmonary vasculature into the bloodstream, where it is rapidly inactivated by combination with hemoglobin (the NO dioxygenation reaction). Therefore, the vasodilatory effects of inhaled NO are limited to these pulmonary therapeutic advantages in the treatment of acute and chronic pulmonary hypertension. Inhaled NO can also be used to prevent ischemia reperfusion injury after percutaneous coronary intervention in adults with heart attacks. Furthermore, inhaled NO can produce systemic anti-inflammatory and anti-platelet effects by increasing the levels of circulating NO biometabolites and by other mechanisms, such as the oxidation of circulating ferrous hemoglobin in the plasma. Finally, NO has known anti-microbial activity.

BRIEF SUMMARY

The present disclosure provides systems and methods for producing nitric oxide (NO) to be used in medical applications. Specifically, systems and methods are provided for a NO generator that is capable of generating a desired concentration of pure and safe NO to be provided to a respiratory system for inhalation by a patient.

In one aspect, the present disclosure provides an apparatus for generating nitric oxide including one or more pairs of electrodes, a filter arranged downstream of the electrodes, and a scavenger arranged downstream of the electrodes. The apparatus further includes one or more sensors configured to measure at least one of a flowrate of gas, an oxygen concentration upstream of the electrodes, a nitric oxide concentration downstream of the scavenger, and a nitrogen dioxide concentration downstream of the scavenger, and a controller in communication with the electrodes and the one or more sensors and configured to supply an electrical signal to the electrodes that controls timing and sparking characteristics of the electrodes. The sparking characteristics of the electrodes determine a concentration of nitric oxide generated by the electrodes.

In some embodiments, the electrodes comprise at least one of tungsten carbide, carbon, nickel, iridium, titanium, rhenium, and platinum In some embodiments, the electrodes comprise iridium.

In some embodiments, the scavenger is fabricated from calcium hydroxide.

In some embodiments, the one or more sensors include an airway flowmeter arranged downstream of the electrodes, an oxygen sensor arranged upstream of the electrodes, a nitric oxide sensor arranged downstream of the scavenger, and a nitrogen dioxide sensor arranged downstream of the scavenger.

In some embodiments, an ignition coil is in communication with the controller and the electrodes.

In some embodiments, the controller is further configured to instruct the ignition coil to supply stored electrical energy to the electrodes.

In some embodiments, the electrical signal supplied to the electrodes controls at least one of a number of electrode spark groups per second, a number of individual electrode sparks per spark group, a time between individual electrode sparks, and a pulse duration.

In some embodiments, the controller is further configured to vary at least one of the number of electrode spark groups per second, the number of individual electrode sparks per spark group, the time between individual electrode sparks, and the pulse duration in response to feedback from the one or more sensors.

In some embodiments, the apparatus further comprises a gas pump arranged upstream of the electrodes.

In some embodiments, the one or more sensors provide an indication of inspiration.

In some embodiments, the controller is further configured to supply the electrical signal to the electrodes in response to detecting inspiration.

In some embodiments, the filter is configured to filter particles flowing downstream of the electrodes with a diameter greater than approximately 0.22 micrometers.

In another aspect, present disclosure provides an apparatus for generating nitric oxide to be integrated into a respiratory system having a breathing apparatus, an inspiratory line, and an airway flowmeter arranged on the inspiratory line. The apparatus includes one or more pairs of electrodes in gaseous communication with the inspiratory line, a filter arranged downstream of the electrodes, and a scavenger arranged downstream of the electrodes. The apparatus further includes one or more sensors configured to measure at least one of an oxygen concentration upstream of the electrodes, a barometric pressure, a nitric oxide concentration downstream of the scavenger, and a nitrogen dioxide concentration downstream of the scavenger, and a controller in communication with the electrodes, the one or more sensors, and the airway flowmeter, and configured to supply an electrical signal to the electrodes that controls timing and sparking characteristics of the electrodes. The sparking characteristics of the electrodes determine a concentration of nitric oxide generated by the electrodes.

In some embodiments, the electrodes are arranged between an inlet and an outlet, the outlet is coupled to the inspiratory line.

In some embodiments, the electrodes are at least partially integrated into the inspiratory line.

In some embodiments, the filter is arranged on the inspiratory line.

In some embodiments, the scavenger is arranged on the inspiratory line.

In some embodiments, the electrodes comprise at least one of tungsten carbide, carbon, nickel, iridium, titanium, rhenium, and platinum.

In some embodiments, the electrodes comprise iridium.

In some embodiments, the scavenger is fabricated from calcium hydroxide.

In some embodiments, the one or more sensors include an oxygen sensor arranged upstream of the electrodes, a nitric oxide sensor arranged downstream of the scavenger, and a nitrogen dioxide sensor arranged downstream of the scavenger.

In some embodiments, an ignition coil is in communication with the controller and the electrodes.

In some embodiments, the controller is further configured to instruct the ignition coil to supply stored electrical energy to the electrodes.

In some embodiments, the electrical signal supplied to the electrodes controls at least one of a number of electrode spark groups per second, a number of individual electrode sparks per spark group, a time between individual electrode sparks, and a pulse duration.

In some embodiments, the controller is further configured to vary at least one of the number of electrode spark groups per second, the number of individual electrode sparks per spark group, the time between individual electrode sparks, and the pulse duration in response to feedback from the one or more sensors.

In some embodiments, the apparatus further comprises a gas pump arranged upstream of the electrodes.

In some embodiments, the airway flowmeter provides an indication of inspiration.

In some embodiments, the controller is further configured to supply the electrical signal to the electrodes in response to detecting inspiration.

In some embodiments, the filter is configured to filter particles flowing downstream of the electrodes with a diameter greater than approximately 0.22 micrometers.

In some embodiments, the breathing apparatus comprises one of a ventilator system, a continuous positive airway pressure (CPAP) system, a high frequency oscillatory ventilator (HFOV), a face mask, a nasal cannula, or an inhaler.

In still another aspect, the present disclosure provides an apparatus for generating nitric oxide to be integrated into a respiratory system having a breathing apparatus and an inspiratory line. The apparatus includes a chamber having a chamber inlet and at least one or more pairs of electrodes arranged within the chamber, a main chamber configured to provide a fluid path to an airway of a patient. The apparatus further includes a filter arranged downstream of the electrodes, a scavenger arranged downstream of the electrodes, and one or more sensors configured to measure at least one of an oxygen concentration upstream of the electrodes, a barometric pressure, a nitric oxide concentration downstream of the scavenger, and a nitrogen dioxide concentration downstream of the scavenger. The apparatus further includes a controller in communication with the electrodes and the one or more sensors. The controller is configured to supply an electrical signal to the electrodes that controls timing and sparking characteristics of the electrodes. The chamber is in communication with the main chamber and gas in the chamber is non-mechanically introduced into the main chamber.

In some embodiments, the main chamber includes a venturi.

In some embodiments, the apparatus further comprises a passage connecting the chamber to the venturi of the main chamber.

In some embodiments, a flow of gas through the venturi is configured to draw a vacuum on the chamber.

In some embodiments, the apparatus further comprises a pre-scavenger arranged upstream of the chamber inlet.

In some embodiments, the apparatus further comprises a pre-filter arranged upstream of the chamber inlet.

In some embodiments, the main chamber and the chamber define a parallel path.

In yet another aspect, the present disclosure provides a method of generating nitric oxide in a respiratory system having a breathing apparatus in communication with an airway of a patient. The method includes coupling a nitric oxide generator having a pair of electrodes to the airway of the patient, triggering the nitric oxide generator to produce a desired concentration of nitric oxide gas, and determining desired sparking characteristics of the electrodes to produce the desired concentration of nitric oxide gas. The method further includes once the sparking characteristics have determined, supplying an electrical signal to the electrodes that initiates the desired sparking characteristics between the electrodes to generate the desired concentration of nitric oxide gas in a flow of gas provided to the airway of the patient.

In some embodiments, triggering the nitric oxide generator to produce a desired concentration of nitric oxide gas comprises monitoring at least one of a gas flowrate provided to the patient, a temperature of gas provided to the patient, and a pressure of gas provided to the patient, detecting a change in at least one of the gas flowrate provided to the patient, the temperature of gas provided to the patient, and the pressure of gas provided to the patient, and determining that the change detected is indicative of an inspiratory event.

In some embodiments, the method further comprises filtering particulates in the flow of gas provided to the patient.

In some embodiments, the method further comprises scavenging at least one of nitrogen dioxide and ozone in the flow of gas provided to the patient.

In some embodiments, determining desired sparking characteristics of the electrodes comprises measuring an atmospheric pressure, and determining a number of electrode spark groups per second, a number of individual electrode sparks per spark group, a time between individual electrode sparks, and a pulse duration.

In some embodiments, the method further comprises monitoring a nitric oxide concentration downstream of the electrodes, determining that the nitric oxide concentration is not equal to the desired concentration of nitric oxide, and in response to determining that the nitric oxide concentration downstream of the electrodes is not equal to the desired nitric oxide concentration, varying via the electrical signal, at least one of a number of electrode spark groups per second, a number of individual electrode sparks per spark group, a time between individual electrode sparks, and a pulse duration.

In some embodiments, the method further comprises monitoring a nitrogen dioxide concentration downstream of the electrodes, determining that the nitrogen dioxide concentration is greater than a pre-defined maximum concentration, and upon determining that the nitrogen dioxide concentration downstream of the electrodes is greater than the pre-defined maximum concentration, ceasing the supplying of the electrical signal to the electrodes.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

The use of the terms "downstream" and "upstream" herein are terms that indicate direction relative to the flow of a gas. The term "downstream" corresponds to the direction of gas flow, while the term "upstream" refers to the direction opposite or against the direction of gas flow.

Currently, administration of inhaled nitric oxide (NO) therapy requires the use of heavy compressed gas cylinders, a gas cylinder distribution network, a complex delivery device, gas monitoring and calibration devices, and trained respiratory therapy staff. These requirements for administering NO therapy present a significant cost to the institution (e.g., a hospital) administering the NO therapy and, therefore, to the patient receiving the NO therapy. For many institutions, inhaled NO therapy can be one of the most expensive drugs used in neonatal medicine. The use of bulky gas cylinders and the expense of inhaled NO therapy result in inhaled NO therapy not being available in most of the world and it is not available for outpatient use.

Several methods have been attempted to produce NO for biomedical purposes, such as, chemically preparing NO from $N_2O_4$ requiring extensive scavenging with antioxidants. Various electrical systems have also been attempted, such as, pulsed arc, gliding arc, dielectric barrier, microwave, corona, radio frequency induced coupled discharge, and non-thermal atmospheric pressure high-frequency plasma discharge. However, these systems and methods produce large amounts of harmful byproducts (e.g., nitrogen dioxide ($NO_2$) and ozone ($O_3$)) and require complex purification systems.

Due to the current difficulties in administering and generating NO for inhalation therapy, it would be desirable to have a lightweight and economical NO generator that can be used for NO inhalation therapy at the bedside of a patient or in portable applications. It would also be desirable to have the NO generator be easily coupled to or integrated into current ventilator systems. It is advantageous from a safety perspective to have the NO that is generated be as clean as possible, so that even in the event that a scavenger fails or is exhausted, the NO that is delivered to a patient is not contaminated with $NO_2$ or $O_3$.

Figure 1:
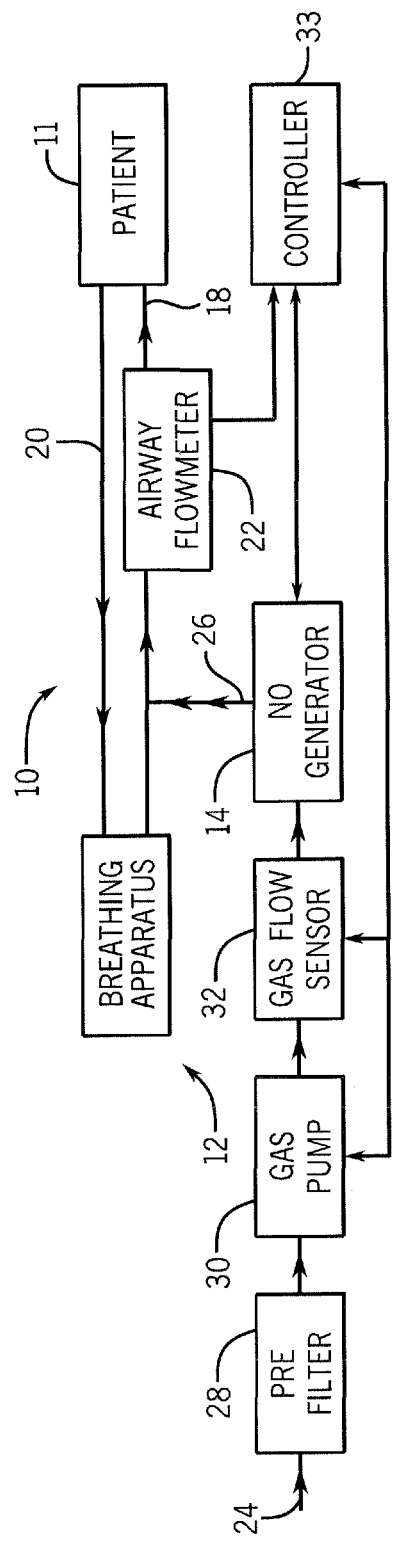
FIG. 1 shows a schematic illustration of a respiratory system according to one embodiment of the present invention.

FIG. 1 shows a respiratory system 10 for administering NO to a patient 11 according to one non-limiting example of the present disclosure. The respiratory system 10 includes a breathing apparatus 12 and a NO generator 14. In some non-limiting examples, the breathing apparatus 12 can be a ventilator system, a continuous positive airway pressure (CPAP) system, a High Frequency Oscillatory Ventilator (HFOV), a face mask, a nasal cannula or an inhaler. The breathing apparatus 12 is configured to enable the passage of gas to and from an airway of the patient 11. In some non-limiting examples, the breathing system 12 can provide mechanical ventilation (i.e., positive pressure to inflate the patient's 11 lungs) to the patient. In other non-limiting examples, the patient 11 may be breathing on their own and the breathing system 12 can provide a flow path to the airway of the patient 11. The illustrated breathing system 12 includes an inspiratory line 18, an expiratory line 20, and an airway flowmeter 22 coupled to the inspiratory line 18. The ventilator 16 can be a commercially available mechanical ventilator used in biomedical applications (e.g., inhalation therapy). As is known in the art, the mechanical ventilator 16 is configured to provide a flow of gas (e.g., air or a nitrogen/oxygen gas mixture) via the inspiratory line 18 to the respiratory tract of the patient 11. Subsequently, the ventilator 16 is configured to remove a flow of gas (e.g., exhaled gas) via the expiratory line 20 from the respiratory tract of the patient 11. In this way, the ventilator 16 can simulate the breathing process for the patient 11. The airway flowmeter 22 measures the flowrate of gas in the inspiratory line 18. In one non-limiting example, the airway flowmeter 22 may control a timing and amount of NO that is synthesized from spark plasma discharge in the NO generator 14.

The NO generator 14 is arranged between an inlet 24 and an outlet 26. Gas (e.g., air or a nitrogen/oxygen gas mixture) is drawn into the NO generator 14 at the inlet 24. The NO generator 14 is configured to generate a predetermined concentration of NO to be inhaled by the patient 11, as will be described in detail below. The NO containing gas is furnished from the NO generator 14 to the outlet 26. The outlet 26 communicates with the inspiratory line 18 of the breathing apparatus 12 upstream of the airway flowmeter 22.

The respiratory system 10 includes a pre-filter 28, a gas pump 30, a gas flow sensor 32 all arranged upstream of the NO generator 14. The pre-filter 28 is arranged downstream of the inlet 24 and upstream of the gas pump 30. The gas flow sensor 32 is arranged downstream of the gas pump 30 and upstream of the NO generator 14. In one non-limiting example, the pre-filter 28 can be configured to filter particles, water droplets and bacteria with a diameter larger than approximately 0.22 micrometers ($\mu m$). It should be known that the particle size filtered by the pre-filter 28 is not meant to be limiting in any way, and alternative pre-filters that filter different particle sizes are within the scope of the present disclosure. In other non-limiting examples, the pre-filter 28 may be removed if the fluid provided at the inlet 24 is be pre-treated (i.e., filtered and dried). In some embodiments, a pre-scavenger (not shown) can be arranged upstream of the pre-filter 28 to remove, for example, $CO_2$ from the inlet gas. Removing $CO_2$ from the inlet gas negates the need for the scavenging $CO_2$ in the gas output from the NO generator 14.

The gas pump 30 is configured to draw gas from inlet 24 and furnish the gas under an increased pressure towards NO generator 14 and through the outlet 26. It should be known that, in other non-limiting examples, the gas pump 30 can be replaced by a fan or a bellows type device. The gas flow sensor 32 is configured to measure a flowrate of gas flowing from the gas pump 30 to the NO generator 14. A controller 33 is in communication with the NO generator 14, the gas pump 30, the gas flow sensor 32 and the airway flowmeter 22. The controller 33 is configured to control the operation of the NO generator 14 and the gas pump 30, as will be described in detail below.

Figure 2:
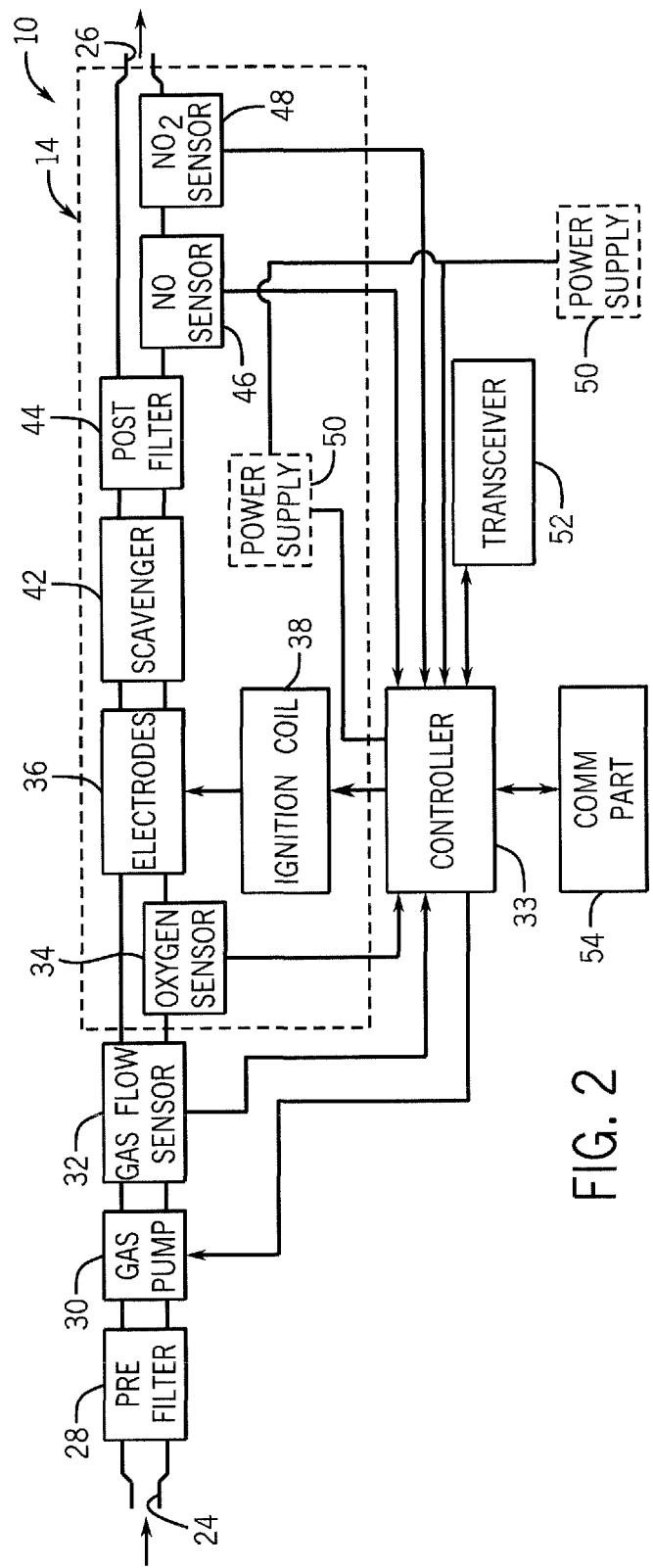
FIG. 2 shows a detailed schematic of a nitric oxide generator in the respiratory system of FIG. 1 according to one embodiment of the present disclosure.

As shown in FIG. 2, the NO generator 14 includes an oxygen sensor 34 arranged upstream of electrodes 36. The oxygen sensor 34 measures an oxygen concentration in the gas being supplied, via the gas pump 30, to the electrodes 36. In some non-limiting examples, the electrodes 36 can include one or more pairs of individual electrodes that can be fabricated from or plated with tungsten carbide, carbon, nickel, iridium, titanium, platinum, rhenium, or an alloy of the aforementioned materials. In one exemplary non-limiting example, the electrodes 36 are fabricated from or plated with iridium because, as described below, iridium can produce a lower concentration of $NO_2$ relative to the concentration of NO generated which is an important safety factor of the NO generator 14.

An ignition coil 38 is in communication with the electrodes 36 and is configured to store and release electrical energy. The energy stored by the ignition coil 38 is delivered to the electrodes 36 to create a plasma in a gap between the electrodes 36. The plasma generated between the electrodes 36 generates NO, as long as nitrogen and oxygen are present in the gas being supplied to the electrodes 36. The controller 33 is in communication with the ignition coil 38 and is configured to control when the ignition coil 38 delivers the stored energy and, therefore, control when the electrodes 36 spark (i.e., form a plasma and generate NO). It should be known that, in some non-limiting examples, the controller 33 can be combined with the NO generator 14 into a single, portable unit.

Downstream of the electrodes 36, the NO generator 14 includes a scavenger 42, a post-filter 44, a NO sensor 46, and a $NO_2$ sensor 48. The post-filter 44 is arranged upstream of the NO and $NO_2$ sensors 46 and 48, and downstream of the scavenger 42. The scavenger 42 is configured to remove harmful byproducts (e.g., $NO_2$ and $O_3$) produced in the plasma created by sparking the electrodes 36. In one non-limiting example, the scavenger 42 can be fabricated from calcium hydroxide $(Ca(OH)_2)$. The post-filter 44 is configured to filter particles (e.g., fragments from the scavenger 42 and/or particles that break off from the electrodes 36 during sparking) in the fluid flowing from the electrodes 36 to the outlet 26. This can prevent the patient 11 from inhaling particle-laden gas and from inhaling electrode particles that boil off due to high temperatures during sparking. In one non-limiting example, the post-filter 44 can be configured to filter particles with a diameter larger or smaller than approximately 0.22 µm. It should be known that the particle size filtered by the post-filter 44 is not meant to be limiting in any way, and alternative post-filters that filter different particle sizes are within the scope of the present disclosure. However, the particle size filtered by the post-filter 44 should be sufficiently small to maintain the safety and health of the patient 11.

The NO sensor 46 measures a concentration of NO in the gas flowing from the electrodes 36 to the outlet 26, and the $NO_2$ sensor 48 measures a concentration of $NO_2$ in the fluid flowing from the electrodes 36 to the outlet 26.

With continued reference to FIG. 2, the controller 33 receives input power from a power supply 50. In one non-limiting example, the power supply 50 can be external to the NO generator 14 (e.g., wall power). In another non-limiting example, the power supply 50 can be integrated into the NO generator 14. In this non-limiting example, the power supply 50 can be in the form of a battery or a rechargeable battery. The controller 33 includes a transceiver 52 and a communication port 54. The controller 33 can be configured to communicate wirelessly, via the transceiver 52, with an external processor (not shown) and/or a display (not shown) using Bluetooth®, WiFi, or any wireless communication protocol known in the art or developed in the future. Alternatively or additionally, the controller 33 can be configured to communicate, via the communication port 54, with the external processor (not shown) and/or the display (not shown) using a universal serial bus (USB) connection, an Ethernet connection, or any wired communication protocol known in the art or developed in the future.

The controller 33 is in communication with the gas pump 30, the gas flow sensor 32, the oxygen sensor 34, the NO sensor 46 and the $NO_2$ sensor 48. In operation, the controller 33 is configured to control a displacement (i.e., a flowrate of gas from the inlet 24 to the outlet 26) of the gas pump 30. For example, a desired flowrate of 5 liters/minute (L/min) can be input to the controller 33 by the external processor. In this non-limiting example, the controller 33 can adjust the displacement of the gas pump 30 in response to the flowrate measured by the gas flow sensor 32 to attempt to maintain the flowrate within a predefined margin of approximately 5 L/min.

Figure 3:
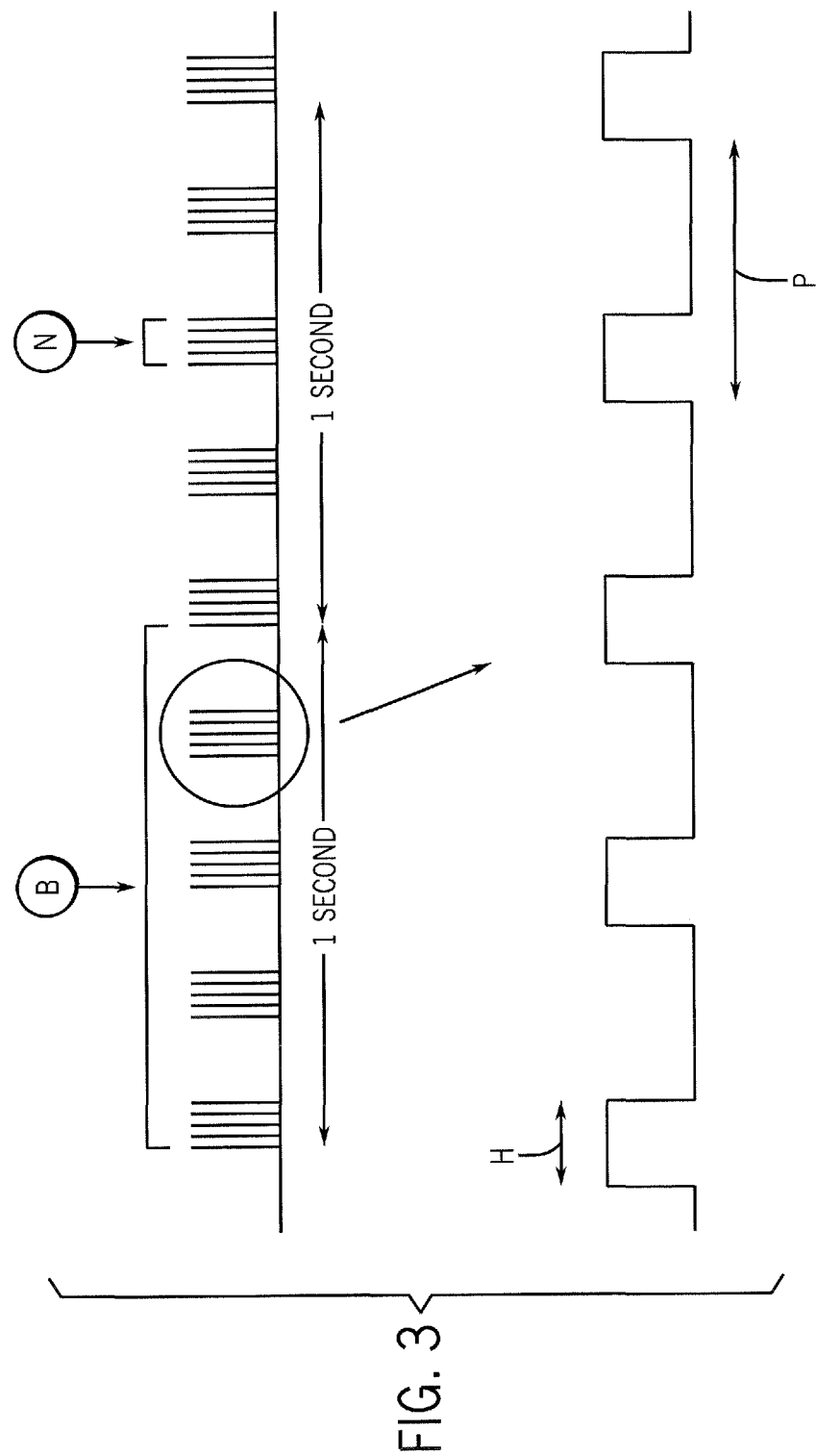
FIG. 3 shows an electrical signal applied to electrodes of the nitric oxide generator of FIG. 2 according to one embodiment of the present disclosure.

The concentrations measured by the oxygen sensor 34, the NO sensor 46, and the $NO_2$ sensor 48 are communicated to the controller 33. In operation, the controller 33 is configured to vary the timing and the sparking characteristics of the electrodes 36 in response to the measurements of the oxygen sensor 34, the NO sensor 46 and the $NO_2$ sensor 48 and the airway flowmeter 22. In one non-limiting example, the timing of the electrodes 36 can be with respect to inspiration of the patient 11. As shown in FIG. 3, the controller 33 is configured supply an electrical signal to the ignition coil 38 and thereby to the electrodes 36 that comprises a plurality of square waves. In the non-limiting example shown in FIG. 3, the electrical signal supplied to the electrodes 36 by the controller 33 can include groups of square waves where each individual square wave in the respective group represents a spark of the electrodes 36. In this non-limiting example, the controller 33 can be configured to control a number spark groups per second (B), a number of individual sparks per group (N), a time between individual sparks (P), and a pulse duration of each individual square wave in the group (H).

Varying the values of B, N, P, and H can alter concentrations of NO and $NO_2$ generated by the NO generator 14, as will be described in detail below. The data gathered from varying B, N, P, and H can be used to develop a theoretical model for generating a given concentration of NO. The theoretical model can be further refined by testing the NO generator 14 at different oxygen concentrations, pressures, humidities, and temperatures. Then, knowing the oxygen concentration, pressure, temperature, and/or humidity of the fluid flowing to the electrodes 36, the controller 33 can calculate an ideal B, N, P, and H to generate a desired concentration of NO. The NO sensor 46 monitors the concentration of NO produced and provides feedback to the controller 33 which, in response to the concentration of NO produced deviating from a desired concentration, can alter the values of B, N, P, and/or H accordingly.

In one non-limiting example, the oxygen concentration of the gas provided to the electrodes 36 may be a constant, known value (e.g., air with 21% $O_2$) which is input to the controller 33. In this non-limiting example, the oxygen sensor 34 may be omitted from the NO generator 14. Alternatively or additionally, a pressure sensor (not shown) can be arranged upstream of the electrodes 36 to measure ambient pressure. As described below, the amount of NO produced by the NO generator 14 can be a function of atmospheric pressure. In one non-limiting example, the controller 33 can be configured to adjust the sparking characteristics of the electrodes 36 in response to the pressure measured by the pressure sensor. Alternatively or additionally, the controller 33 can be configured to monitor a condition, or health, of the scavenger 42 by determining if the concentration of $NO_2$, measured by the $NO_2$ sensor 48, exceeds a pre-determined value. If the $NO_2$ concentration exceeds the pre-determined value, the scavenger 42 may be exhausted and the controller 33 can cease the sparking of the electrodes 36 and instruct a user of the NO generator 14 to replace the scavenger 42. Alternatively or additionally, a colorimetric pH sensor can estimate exhaustion of the scavenger 42.

In operation, the NO generator 14 is configured to produce therapeutic concentrations of NO, for example, between approximately 5 and 80 parts per million (ppm) by pulsed sparking of the electrodes 36. The therapeutic concentrations of NO produced by the NO generator 14 can be supplied to the inspiratory line 18 and thereby to the patient 11. Thus, the NO generator 14 does not require the use of valves to enable the flow of NO laden gas to the patient 11. In one non-limiting example, the electrodes 36 of the NO generator 14 can be triggered, by the controller 33, to spark continuously. In another non-limiting example, the electrodes 36 of the NO generator 14 can be triggered, by the controller 33, to spark during or prior to inspiration of the patient 11. Triggering the electrodes 36 during or prior to inspiration can avoid waste NO generated during exhalation, and can enable the NO generator 14 to demand less power when compared with continuous operation.

The controller 33 can be configured to detect inspiration of the patient 11 based on the flowrate measured by the airway flowmeter 22, a temperature in the inspiratory line 18, a temperature in the expiration line 20, a pressure in the inspiratory line 18, and/or a pressure in the expiration line 20. The theoretical model executed by the controller 33 for determining the values of B, N, P, and H for a desired NO concentration can be adjusted whether the electrodes 36 are being sparked continuously or intermittently (i.e., triggered during or prior to inspiration).

Figure 4:
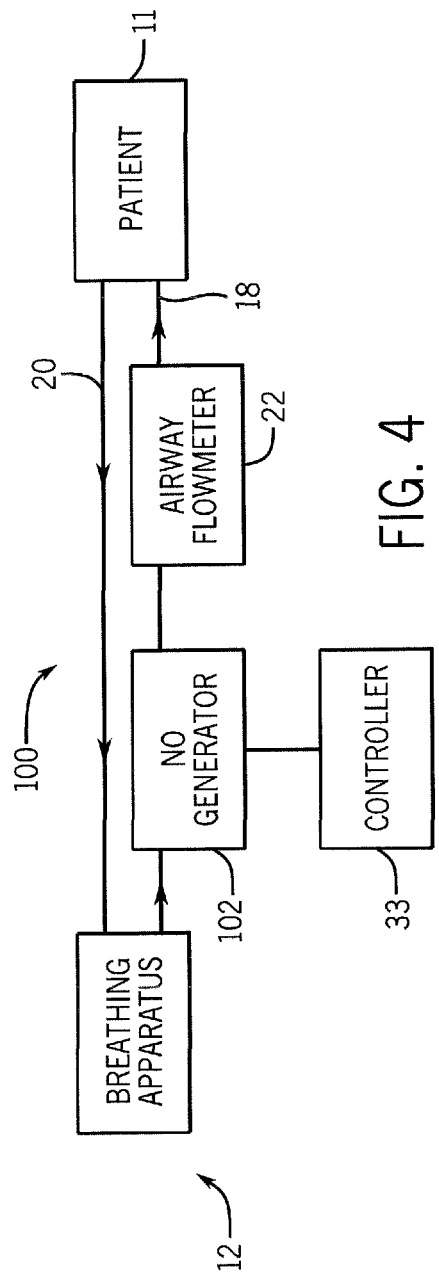
FIG. 4 shows a schematic illustration of a respiratory system according to another embodiment of the present invention.

FIG. 4 shows a schematic illustration of a respiratory system 100 according to another non-limiting example of the present disclosure. The respiratory system 100 of FIG. 4 is similar to the respiratory system 10 of FIG. 1 except as described below or is apparent from FIG. 4. As shown in FIG. 4, the respiratory system 100 includes a NO generator 102 integrated into the inspiratory line 18 of the breathing apparatus 12. With the NO generator 102 integrated into the inspiratory line 18, the respiratory system 100 may not include the pre-filter 28, the gas pump 30, and the gas flow sensor 32, as the ventilator 16 provides the flow of gas to the NO generator 102.

Figure 5:
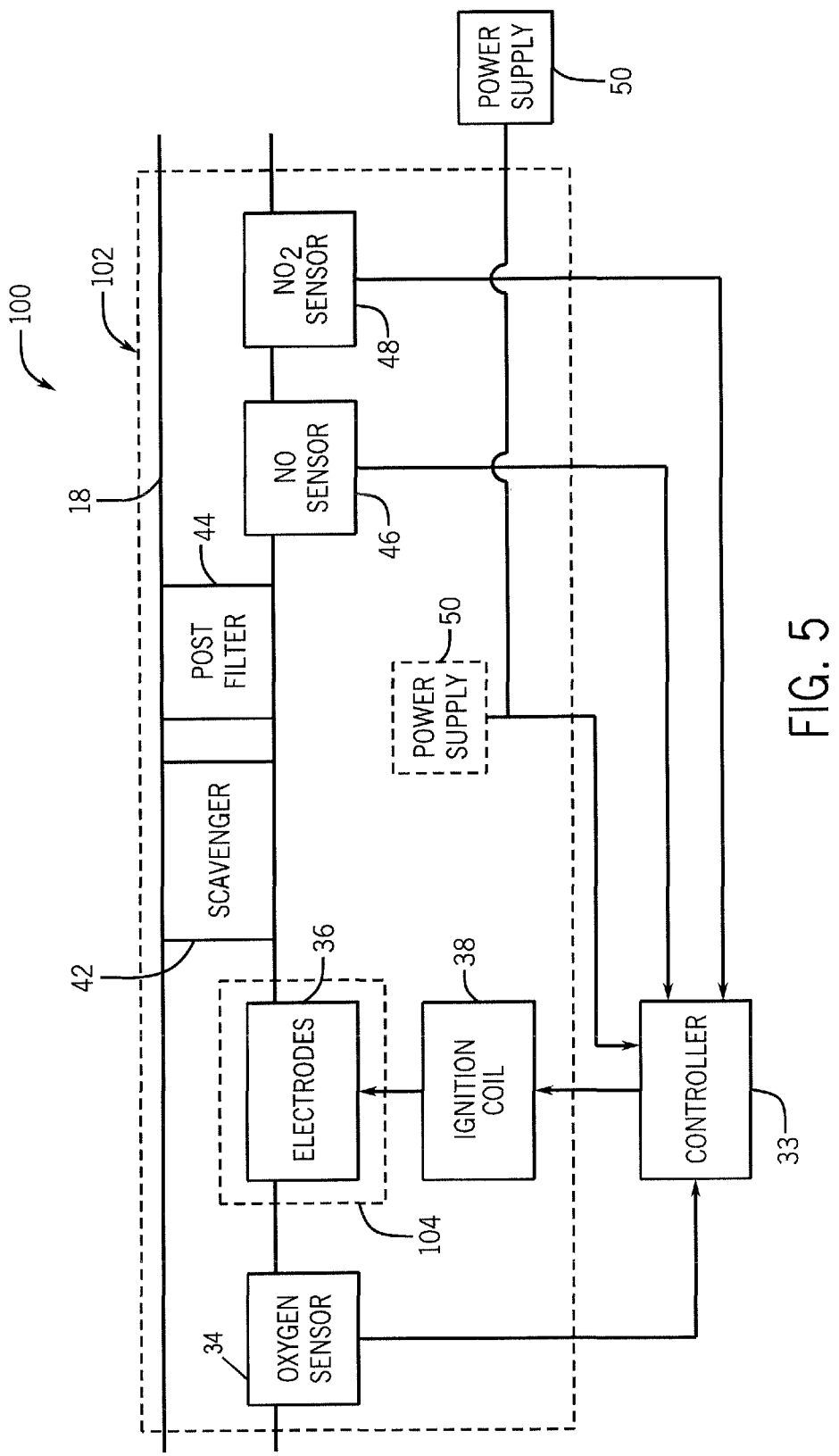
FIG. 5 shows a detailed schematic of a nitric oxide generator in the respiratory system of FIG. 4 according to another embodiment of the present disclosure.

The NO generator 102 of FIG. 5 is similar to the NO generator 14 of FIG. 1 except as described below or is apparent from FIG. 5. As shown in FIG. 5, the scavenger 42, the post-filter 44, the NO sensor 46 and the $NO_2$ sensor are integrated into the inspiratory line 18, and the NO generator 102 includes a membrane 104 surrounding or covering the electrodes 36. The membrane 104 protects the electrodes 36 from any water droplets or mucous in the inspiratory line 18 while allowing the gas flowing through the inspiratory line 18 (e.g., air or a nitrogen/oxygen gas mixture) to freely pass through the membrane 104. In one non-limiting example, the membrane 104 can be a microporous polytetrafluoroethylene (PTFE) membrane. It should be known that the electrodes 36 do not need be completely integrated into the inspiratory line 18, and that only the tips of the electrodes 36 need to be in the gas path defined by the inspiratory line 18.

In operation, placing the NO generator 102 inline with the inspiratory line 18 reduces the transit time of the generated NO gas to the lung of the patient 11. This reduces the probability of the generated NO oxidizing to $NO_2$ prior to reaching the patient 11. Also, placing the NO generator 102 inline with the inspiratory line 18 negates the need for valves to enable the flow of NO laden gas to the patient 11. In one non-limiting example, the controller 33 is configured to intermittently spark the electrodes 36 of the NO generator 102 prior to or during inspiration of the patient 11. Generating NO only during or upon inspiration, compared to continuous sparking of the electrodes 36, enables the NO generator 102 to generate NO during approximately one quarter to one eighth of the total respiratory cycle time of the patient 11. This can reduce the power demanded of the NO generator 102, favor portable applications, avoid generating waste NO, and reduce a necessary size of the scavenger 42.

Figure 6:
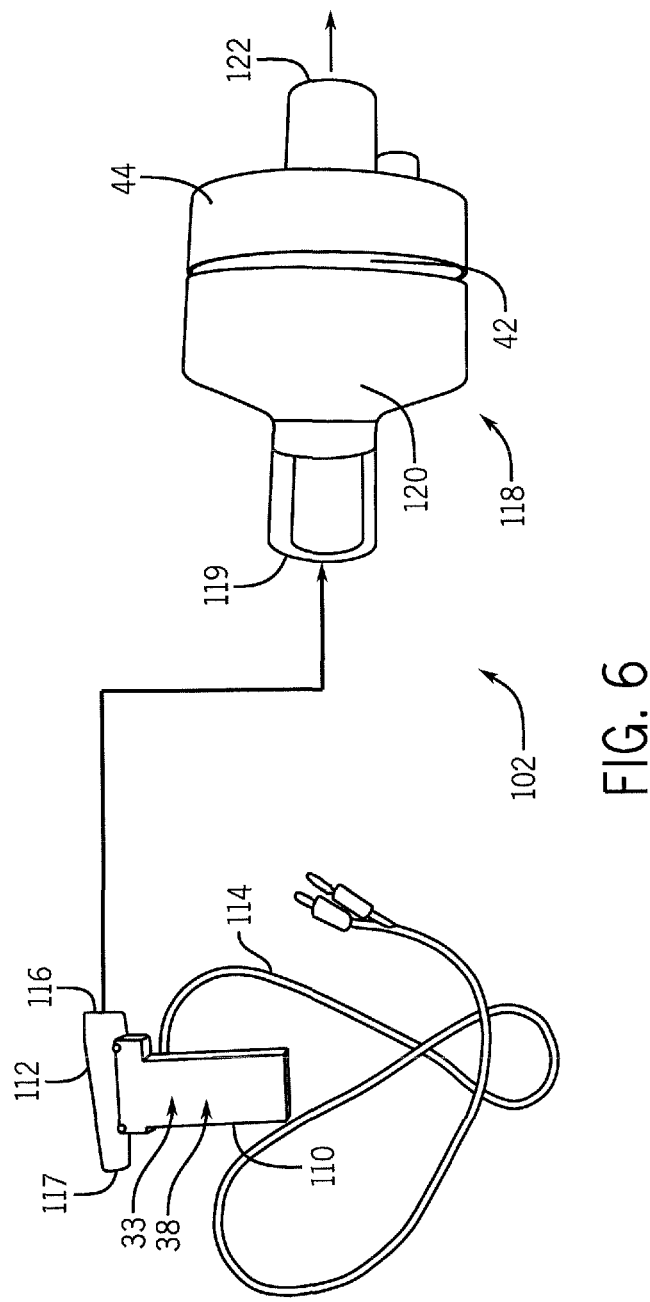
FIG. 6 shows one implementation of the nitric oxide generator of FIG. 5 according to one embodiment of the present disclosure.

FIG. 6 shows one non-limiting implementation of the NO generator 102 where the controller 33 and the ignition coil 38 are enclosed in a base 110. The base 110 is coupled to a tube 112 configured to be placed inline with an inspiratory line of a respiratory system, or breathing apparatus. The electrodes 36 are arranged partially within the base 110 such that the tips of the electrodes 36 are in a fluid path defined by the tube 112. The illustrated NO generator 102 includes a power cord 114 attached to the base 102 to supply power to the controller 33 and the power supply 50. The power cord 114 is detachable from the base 110 to aid in the portability of the NO generator 102.

A first end 116 of the tube 112 is configured to receive a cartridge assembly 118 and a second end 117 of the tube 112 is configured to couple to the inspiratory line 18. The cartridge assembly 118 includes a cartridge inlet 119 configured to couple to the first end 116 of the tube 112, a cartridge 120 arranged upstream of and coupled to the post-filter 44, and a cartridge outlet 122 configured to couple to the inspiratory line 18. In one non-limiting example, the cartridge 120 can be filled with a microporous material (e.g., foam). The scavenger 42 is arranged between the cartridge 120 and the post-filter 44.

Figure 7:
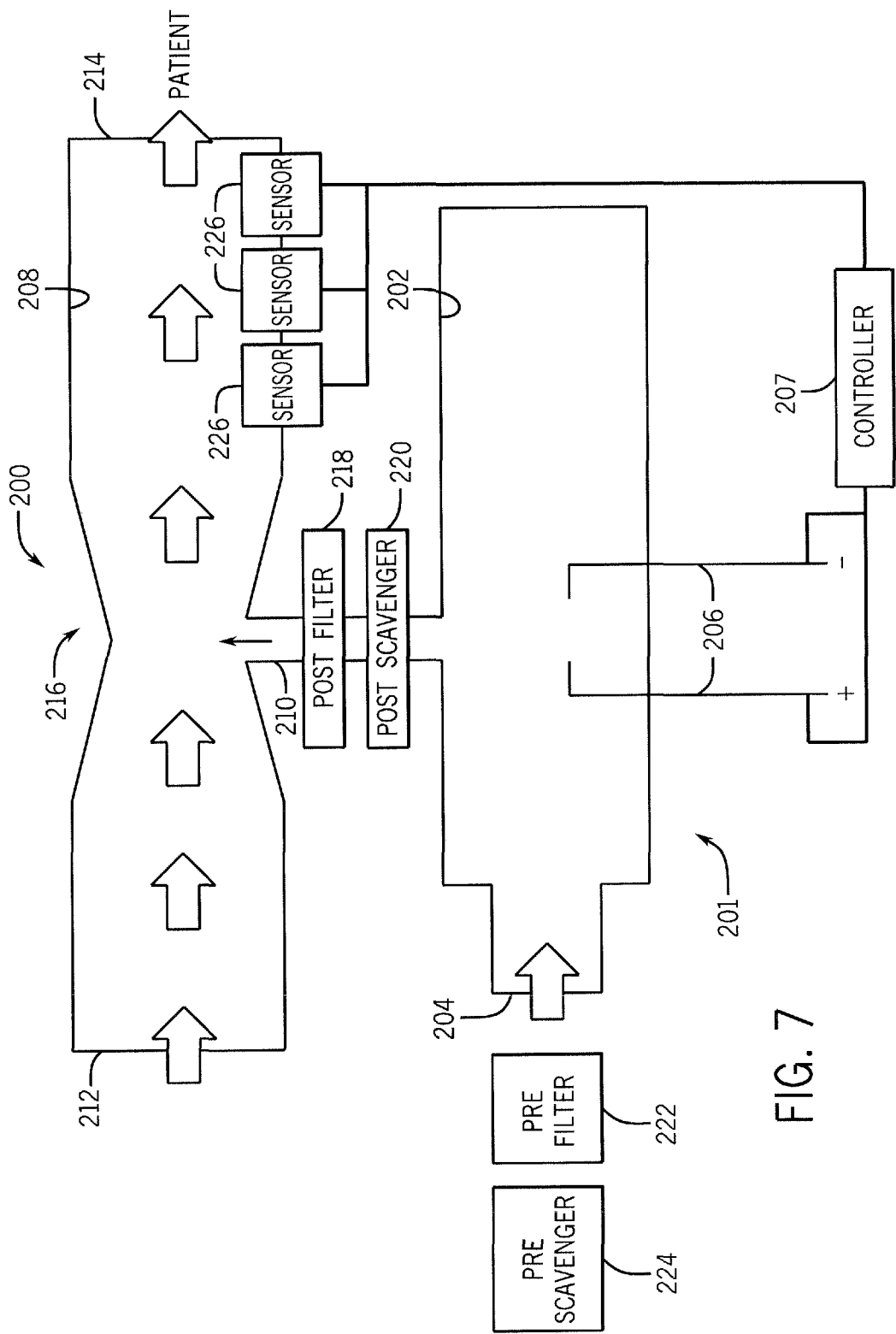
FIG. 7 shows a respiratory system according to yet another embodiment of the present disclosure.

FIG. 7 shows a respiratory system 200 having an NO generator 201 according to another non-limiting example of the present disclosure. As shown in FIG. 7, the NO generator 201 includes a chamber 202 having a chamber inlet 204 arranged upstream of electrodes 206. Similar to the electrodes 36, described above, the electrodes 206 can be powered by a controller 207 which is configured to control when energy is delivered to the electrodes 206 and, therefore, control when the electrodes 206 spark (i.e., form a plasma and generate NO). The chamber 202 is coupled to a main chamber 208 via passage 210. The main chamber 208 includes a main inlet 212, a main outlet 214 and a venturi 216 arranged therebetween. The main outlet 214 is in gas communication with the respiratory tract of a patient. The passage 210 is coupled to the venturi 216 of the main chamber 208 and includes a post-filter 218 and a post-scavenger 220. The post-filter 218 is configured to filter particles (e.g., particles that break off or are vaporized from the electrodes 36 during sparking) in the gas flowing through the passage 210 from the chamber 202 to the main chamber 208. The post-scavenger 220 is configured to remove harmful byproducts (e.g., $NO_2$ and $O_3$) produced in the plasma created by sparking the electrodes 206. In other non-limiting examples, the post-filter 218 and/or the post-scavenger 220 may be arranged in the main chamber 208 downstream of the venturi 216.

In one non-limiting example, a pre-filter 222 may be arranged upstream of the chamber inlet 202 to remove particles and/or water droplets in the fluid being supplied to the chamber inlet 202. Alternatively or additionally, a pre-scavenger 224 may be arranged upstream of the chamber inlet 202 to remove compounds which are potentially harmful to the post-scavenger 220 (e.g., carbon dioxide ($CO_2$)). Pre-scavenging the gas flowing to the electrodes 206 can enable a size of the post-scavenger (not the post-filter) 220 to be reduced. Reducing the size of the post-scavenger 220 by pre-scavenging can, in one non-limiting example, enable the post-scavenger 220 to be placed over a spark gap between the electrodes 206 within a tracheostomy tube or an endotracheal tube to produce NO within the airway, even close to the carina.

One or more sensors 226 are arranged downstream of the venturi 216. The sensors 226 are configured to measure an oxygen concentration, a NO concentration, and/or an $NO_2$ concentration in the gas flowing from the venturi 216 to the main outlet 214. Alternatively or additionally, the chamber 202 may include one or more additional sensors (not shown) to measure at least one of a pressure, a temperature, and a humidity in the chamber 202.

In some non-limiting examples, the main chamber 208, the chamber 202, and/or the passage 210 may include one or more other passages or modules, such as a ventilator gas stream or breathing apparatus.

In operation, the main inlet 212 and the chamber inlet 204 receive a flow of gas (e.g., air or a nitrogen/oxygen gas mixture). The flowrate of gas provided to the main inlet 212 can be sufficiently greater than the flowrate of gas provided to the chamber inlet 204 which causes the flow through the venturi 216 to draw a vacuum on the chamber 202. The vacuum drawn on the chamber 202 can draw fluid from the chamber 202 into the main chamber 208. This operation of the NO generator 201 can obviate the need to control the total amount of NO rich gas injected into the main chamber 208 with one or more valves. Also, the NO generator 201 non-mechanically, (i.e., without the use of a pump or valves) provides the flow of NO laden gas to the patient.

The operation of the controller 207 is similar to the controller 33, described above, and is configured to control the concentration of NO generated by sparking the electrodes 206 by varying B, N, P, and H. The controller 207 can adjust B, N, P, and/or H in response to the measurements by the one or more sensors 226. In one non-limiting example, the desired concentration of NO generated for a particular application can be calculated by the controller 207 based on the mass flowrate of gas through the main chamber 208 and the amount of vacuum drawn on the chamber 202. In some non-limiting examples, the NO generator 201 can include a flow sensor (not shown) in communication with the controller 207 to enable timed inspiratory generation of NO. In this non-limiting example, the controller 207 can be configured to trigger the electrodes 206 to generate NO during or prior to inspiration of the patient which can reduce wear of the electrodes 206, oxidation of NO into $NO_2$, and the power requirements of the NO generator 201.

Figure 8:
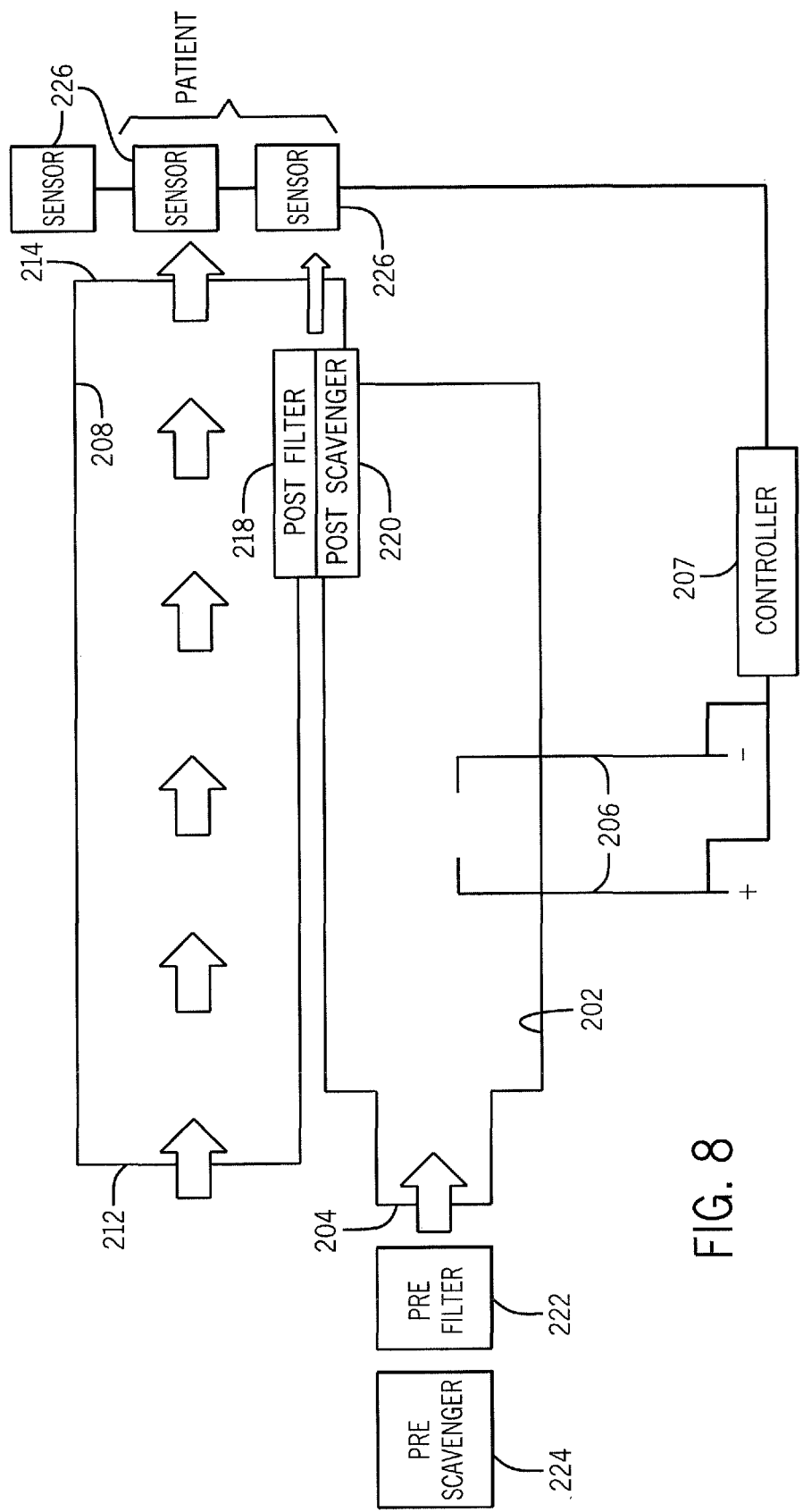
FIG. 8 shows a respiratory system according to still another embodiment of the present disclosure.

FIG. 8 shows a respiratory system 300 having a NO generator 301 according to another non-limiting example of the present disclosure. The NO generator 301 of FIG. 8 is similar to the NO generator 201 of FIG. 7 except as described below or is apparent from FIG. 8. As shown in FIG. 8, the NO generator 301 can employ a proportional parallel delivery. Rather than mixing the gas before it is delivered to the patient, an inspiration can pull NO rich gas from the chamber 202 and fluid from the main chamber 208 from a parallel passage 302. That is, the patient can draw output gas directly from the parallel passage 302 without requiring the use of valves or a pump to furnish the produced NO laden gas to the patient.

Figure 9:
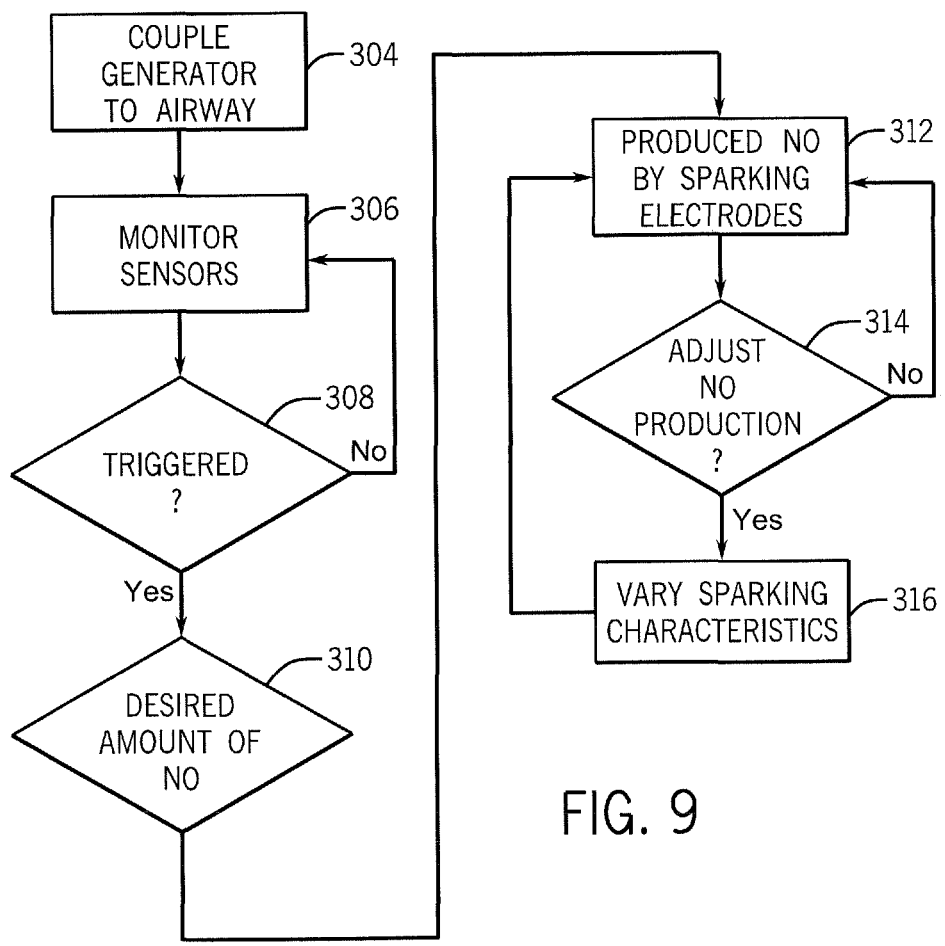
FIG. 9 is a flowchart illustrating steps for operating a respiratory system according to the present disclosure.

As described above, the NO generators 14, 102, 201, and 301 may operate similarly to provide safe and pure NO to a patient's airway. The operation of the respective controller (i.e., controllers 33 and 207) in the respiratory systems 10, 100, 200, and 300 can control the operation of the NO generators 14, 102, 201, and 301. FIG. 9 shows one non-limiting example of the operation of any of the above-described respiratory systems 10, 100, 200, and 300. As shown in FIG. 9, a NO generator (e.g., NO generator 14, 102, 201, and/or 301) is coupled to an airway of a patient at step 304. As described above, the NO generator can be coupled to the airway of the patient, for example via a connection to an inspiration line, a venturi, a parallel path, or the NO generator can be placed inline with an airway of the patient. With the NO generator coupled to the airway of the patient, the controller (e.g., controller 33 or controller 207) monitors sensor inputs to the patient at step 306. In some non-limiting examples, the controller can monitor an oxygen concentration downstream of the NO generator, an ambient pressure, a gas flowrate being provided (mechanically or non-mechanically) to the patient, a NO concentration downstream of the NO generator, and a $NO_2$ concentration downstream of the NO generator.

The controller (e.g., controller 33 or controller 207) then determines at step 308 if the NO generator should be triggered to produce NO to be inhaled by the patient. In some non-limiting examples, the controller can be configured to trigger at or just before an inspiratory event (e.g., by monitoring the gas flow provided to the patient, a pressure in an inspiratory line, a temperatures in an inspiratory line, etc.). In other non-limiting examples, the controller can be manually triggered by a user of the NO generator. Once the NO generator has been triggered by the controller at step 308, the controller can determine the desired sparking characteristics, provided by a pulsed electrical signal, to be sent to electrodes (e.g., electrodes 36 or electrodes 208) at step 310. The controller can be pre-configured to produce a desired concentration of pure and safe NO gas to be inhaled by the patient. In one non-limiting example, the pre-configured concentration of NO gas is determined at step 310 by the controller as a function of the atmospheric pressure and/or the B, N, P, and H electrode spark characteristics, described above. That is, the controller can, based on the measured atmospheric pressure, determine the desired B, N, P, and H of the electrical signal to produce the pre-configured concentration of NO.

With the desired sparking characteristics determined at step 310, the controller sends the corresponding electrical signal to the electrodes and the NO generator produces, at step 312, the pre-configured concentration on pure and safe NO gas by spark plasma discharge to be provided to the airway of the patient. While the NO generator is producing NO gas at step 312, the controller monitors the inputs from the sensors (e.g., an oxygen concentration upstream of the NO generator, an ambient pressure, a gas flowrate being provided (mechanically or non-mechanically) to the patient, a NO concentration downstream of the NO generator, and a $NO_2$ concentration downstream of the NO generator. Based on the inputs from the sensors, the controller determines at step 314 whether or not to adjust the NO production. For example, if controller detects that the output NO gas concentration is not substantially equal to the desired NO gas concentration, the controller can alter the sparking characteristics of the electrodes, at step 316, by varying at least one of B, N, P, and H to bring the produced NO gas concentration in line with the desired NO gas concentration. Alternatively or additionally, if the controller detects an increase in gas flow being provided to the airway of the patient, the controller can alter the sparking characteristics of the electrodes, at step 316 by varying at least one of B, N, P, and H accordingly. Thus, the controller (e.g., controller 33 or controller 207) is configured to alter the sparking characteristics (i.e., a concentration of synthesized NO gas produced by spark plasma discharge between the electrodes) based on the feedback from one or more sensors.

EXAMPLES

The following examples set forth, in detail, ways in which the respiratory systems 100 and 200 and/or the NO generators 14, 102, 201 and 301 may be used or implemented, and will enable one of skill in the art to more readily understand the principle thereof. The following examples are presented by way of illustration and are not meant to be limiting in any way.

Figure 10:
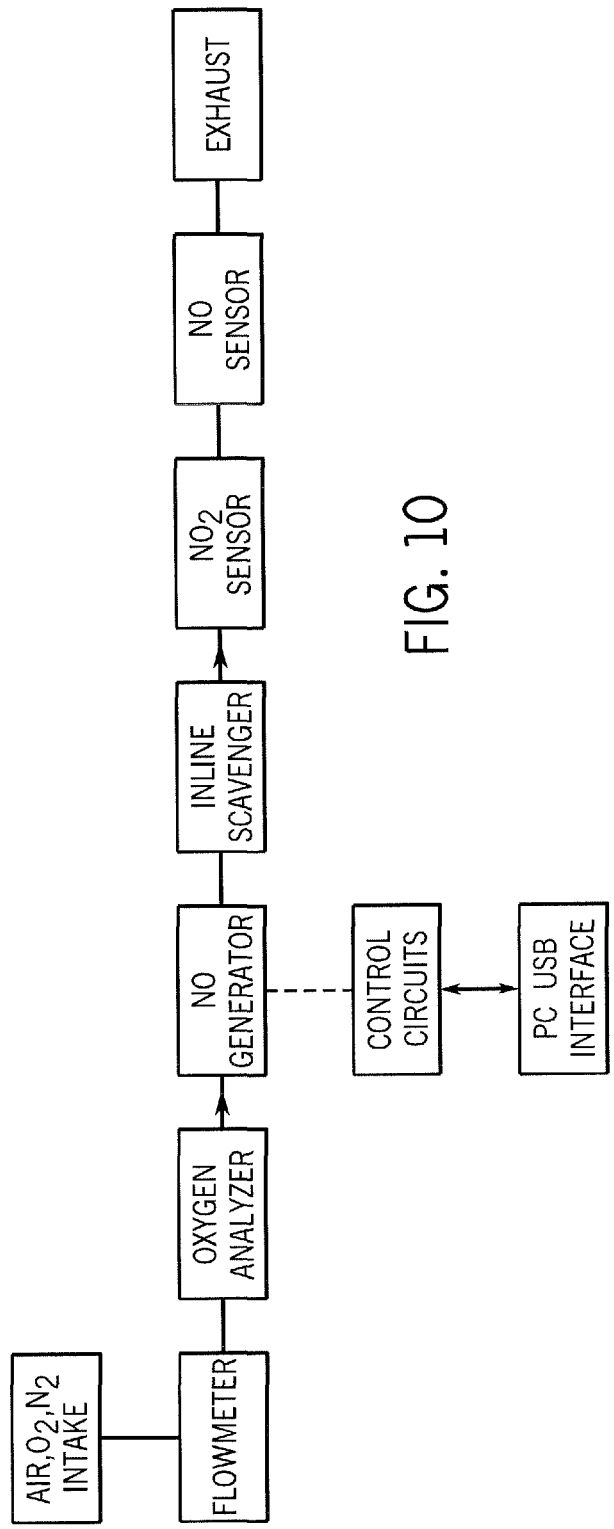
FIG. 10 shows a schematic used for testing a nitric oxide generator according to one embodiment of the present disclosure.
Figure 11:
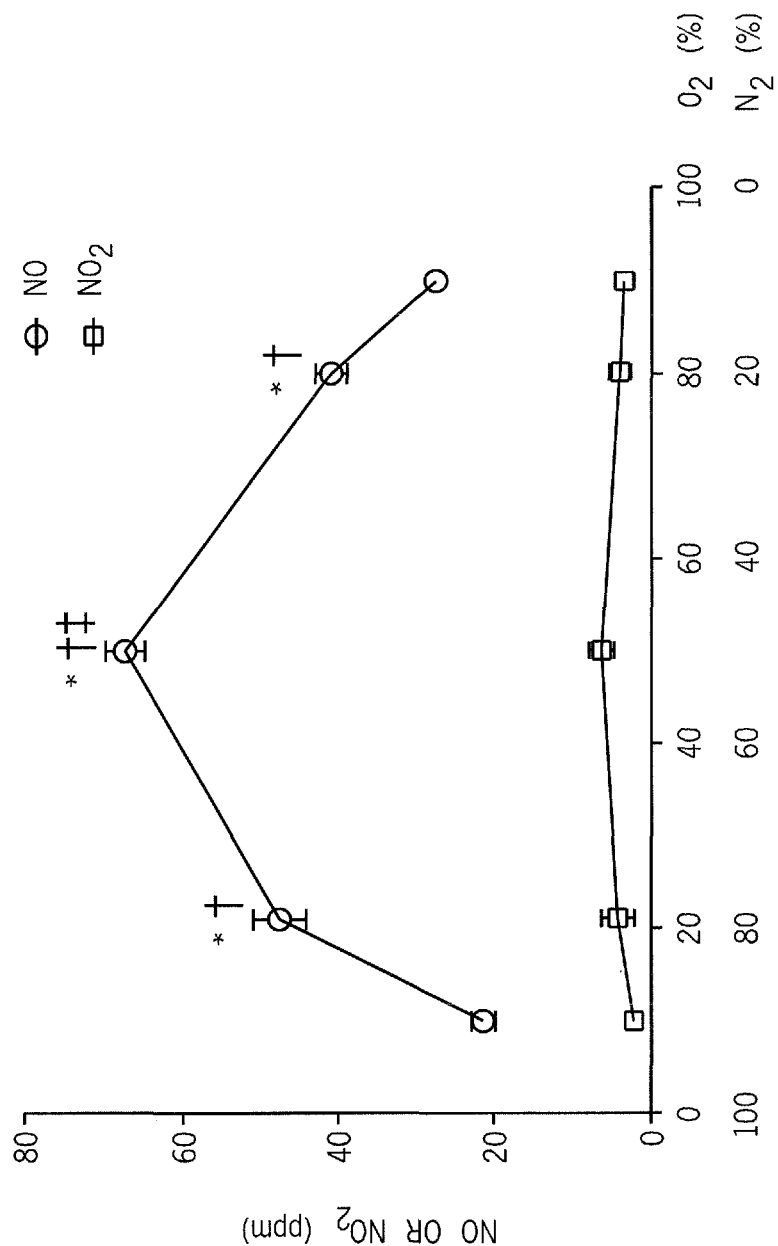
FIG. 11 shows a graph illustrating concentrations of NO and $NO_2$ generated while testing the nitric oxide generator of FIG. 2.

Example 1: Measuring NO and $NO_2$ Generation at Varying Oxygen and Nitrogen Concentrations The NO generator 14 was tested with varying nitrogen and oxygen concentrations being provided to the electrodes 36. The test was performed using the test setup shown in FIG. 10 and at atmospheric pressure. The controller 33 was configured to spark the electrodes 36 using the following settings: B=25; N=35; P=240 μs; and H=100 μs. The NO and $NO_2$ concentrations generated by the NO generator 14 were measured at a constant gas flow of 5 L/min and with oxygen levels of 10%, 21%, 50%, 80%, and 90% and a balanced amount of nitrogen. FIG. 11 shows the concentrations of NO and $NO_2$ generated during the test. As shown in FIG. 11, maximum NO (68±4 ppm) and $NO_2$ (6±2 ppm) concentrations were generated at 50% oxygen. Lower concentrations of NO and $NO_2$ were generated as the oxygen concentration deviated from 50% (i.e., either increasing the oxygen concentration above 50% or decreasing the oxygen concentration below 50%).

Figure 12:
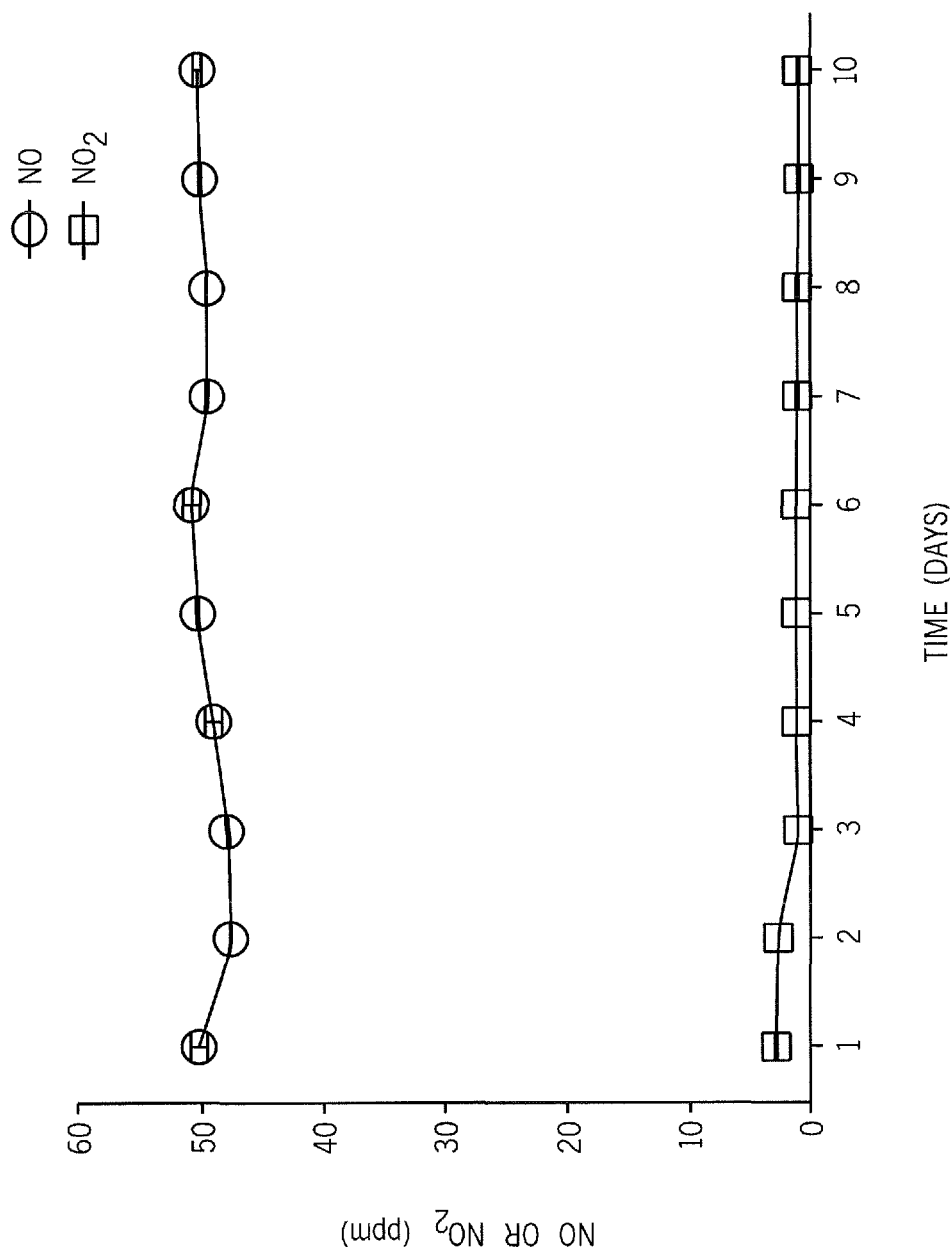
FIG. 12. shows a graph illustrating NO and $NO_2$ concentrations generated by the nitric oxide generator of FIG. 2 over the 10 day test.

Example 2: Measuring the NO and $NO_2$ Concentrations During Continuous Operation for 10 Days The NO generator 14 was tested at an oxygen concentration of 21% (i.e., in air) and a constant gas flow rate of 5 L/min. The electrodes 36 were fabricated from iridium-platinum. The test was performed using the test setup shown in FIG. 10 and at atmospheric pressure. The controller 33 was configured to spark the electrodes 36 using the following settings to produce approximately 50 ppm of NO: B=20, N=20, P=240 μs; and H=70 μs. FIG. 12 shows the NO and $NO_2$ concentrations generated by the NO generator over the 10 day test. As shown in FIG. 12, the NO and $NO_2$ concentrations remained substantially constant over the 10 days.

Example 3: Measuring NO and $NO_2$ Generation at Varying B, N, P, and H

Figure 13B:
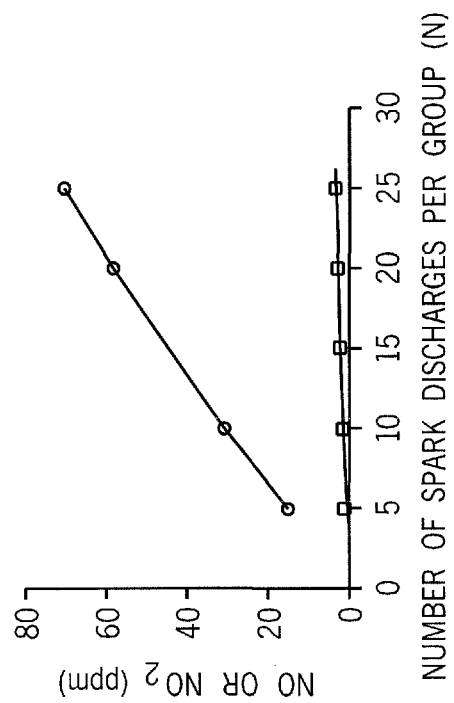
FIG. 13B shows a graph illustrating the effect of varying number of spark discharges per group on NO and $NO_2$ concentration for the nitric oxide generator of FIG. 2.
Figure 13D:
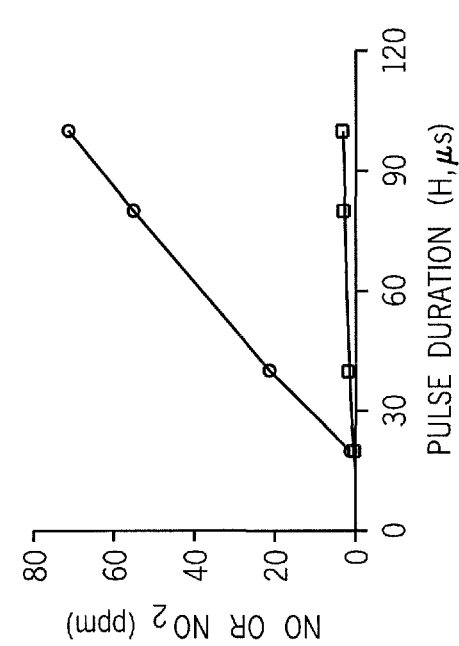
FIG. 13D shows a graph illustrating the effect of pulse duration on NO and $NO_2$ concentration for the nitric oxide generator of FIG. 2.
Figure 13A:
FIG. 13A shows a graph illustrating the effect of varying number of spark groups per second on NO and $NO_2$ concentrationthe nitric oxide generator of FIG. 2.
Figure 13C:
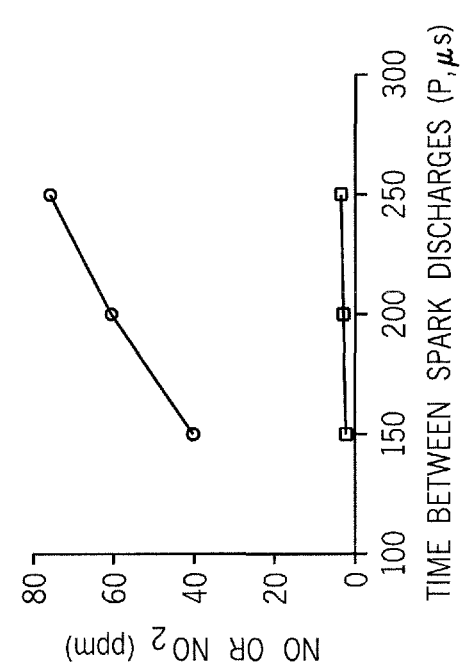
FIG. 13C shows a graph illustrating the effect of varying time between spark discharges on NO and $NO_2$ concentration for the nitric oxide generator of FIG. 2.

As described above, a theoretical model of the NO and $NO_2$ generation at varying B, N, P, and H, can be input to the controller of the respective respiratory system. The NO generator 14 was tested at an oxygen concentration of 21% (i.e., in air) and a constant gas flow rate of 5 L/min. The electrodes were fabricated from iridium-platinum. The test was performed using the test setup shown in FIG. 10 and at atmospheric pressure. FIG. 13A shows the effect of varying B with N=25, P=240 μs, and H=100 μs. As shown in FIG. 13A, the NO and $NO_2$ concentrations generated increased substantially and linearly with increasing values of B. FIG. 13B shows the effect of varying N with B=35, P=240 μs, and H=100 μs. As shown in FIG. 13B, the NO and $NO_2$ concentrations generated increased substantially and linearly with increasing values of N. FIG. 13C shows the effect of varying P with B=35, N=25, and H=100 μs. As shown in FIG. 13C, the NO and $NO_2$ concentrations generated increased substantially and linearly with increasing values of P. FIG. 13D shows the effect of varying H with B=35, N=25, and P=240 μs. As shown in FIG. 13D, the NO and $NO_2$ concentration generated increased substantially and linearly with increasing values of H. The data shown in FIGS. 12A-D indicate that NO production can be precisely controlled (using B, N, P, and H), and that NO production can increase with pulse repetition (B and N) and energy storage capacitance (P and H).

Figure 14:
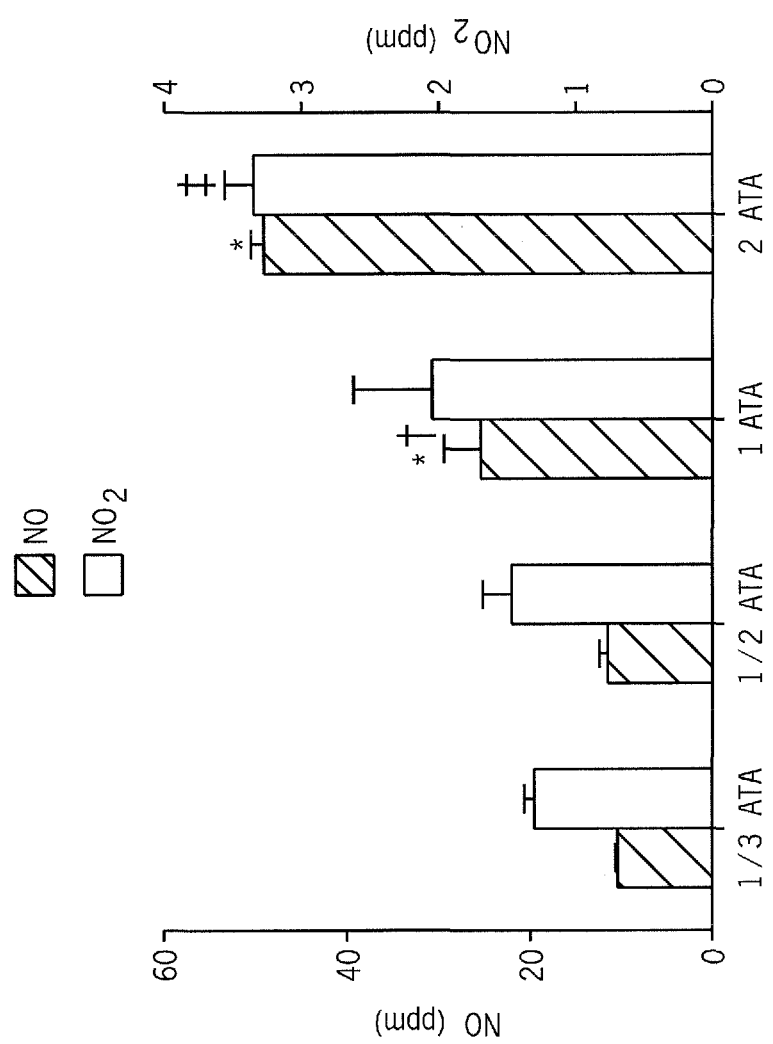
FIG. 14 shows a graph illustrating NO and $NO_2$ concentrations generated by the nitric oxide generator of FIG. 2 at varying atmospheric pressures.

Example 4: Measuring NO and $NO_2$ Generation at Varying Atmospheric Pressure The NO generator 14 was tested at an oxygen concentration of 21% (i.e., in air) in a 500 milliliter chamber. The controller 33 was configured to spark the electrodes 36 using the following settings: B=100, N=10, P=140 μs; and H=10 μs. The NO generator was run for 1 minute and the NO and $NO_2$ concentrations were measured at one-third atmospheres absolute pressure (ATA), one-half ATA, one ATA, and two ATA. FIG. 14 shows the NO and $NO_2$ concentrations at the varying atmospheric pressures. As shown in FIG. 13, compared to NO and $NO_2$ concentrations generated at one ATA, the NO and $NO_2$ production decreased with decreasing ATA and increased with increasing ATA. However, the ration of $NO_2$/NO remained substantially constant for each of the atmospheric pressures tested.

Figure 15:
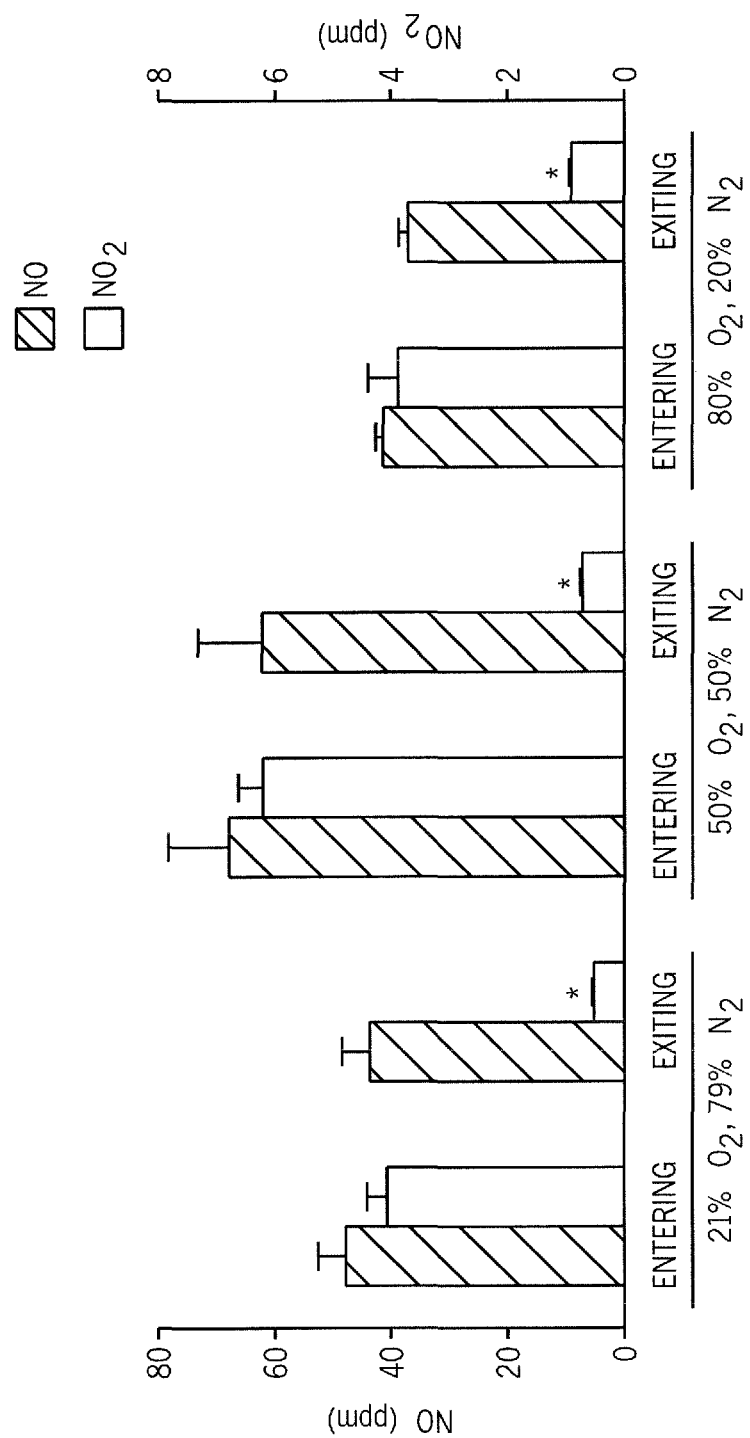
FIG. 15 shows a graph illustrating the NO and $NO_2$ concentrations entering and exiting a scavenger following and in series with the nitric oxide generator of FIG. 2.

Example 5: Measuring NO and $NO_2$ Concentrations Entering and Exiting the Scavenger 42 of the NO Generator 14 at Varying Oxygen and Nitrogen Concentrations The NO generator 14 was tested at a constant gas flow rate of 5 L/min. The electrodes 36 were fabricated from iridium-platinum. The test was performed using the test setup shown in FIG. 10 at atmospheric pressure. The scavenger 42 comprised 72 grams (g) of $Ca(OH)_2$ and the post-filter 44 was placed downstream of the scavenger 42. The controller 33 was configured to spark the electrodes 36 using the following settings: B=25, N=35, P=240 μs; and H=100 μs. The NO and $NO_2$ concentrations generated by the NO generator 14 were measured entering (i.e., upstream) and exiting (i.e., downstream) of the scavenger 42 at oxygen levels of 21% (i.e., air), 50%, and 80%, and a balanced amount of nitrogen. FIG. 15 shows the concentrations of NO and $NO_2$ measured during the test. As shown in FIG. 15, at 21% oxygen (i.e., in air), the NO generator 14 produced 48±5 ppm NO and 44±5 ppm exited the scavenger 42. The NO generator 14 produced 4.1±0.4 ppm $NO_2$ and 0.5±0.03 ppm exited the scavenger 42. At 50% oxygen, the NO generator 14 produced 68±11 ppm NO and 62±11 ppm exited the scavenger 42. The NO generator 14 produced 6.2±0.4 ppm $NO_2$ and 0.7±0.02 ppm exited the scavenger 42. At 80% oxygen, the NO generator 14 produced 41±1 ppm NO and 37±2 ppm exited the scavenger 42. The NO generator 14 produced 3.9±0.5 ppm $NO_2$ and 0.9±0.04 ppm exited the scavenger 42. Thus, the scavenger 42 removed between approximately 87% and 95% of the $NO_2$ produced by the NO generator 14. These results demonstrate that the scavenger 42 is highly efficient at removing $NO_2$ (to below the Environmental Protection Agency (EPA) limit after scavenging) without reducing the NO concentrations.

Example 6: Measuring NO and $NO_2$ Concentrations Entering and Exiting the Scavenger 42 of the NO Generator 102

Figure 16:
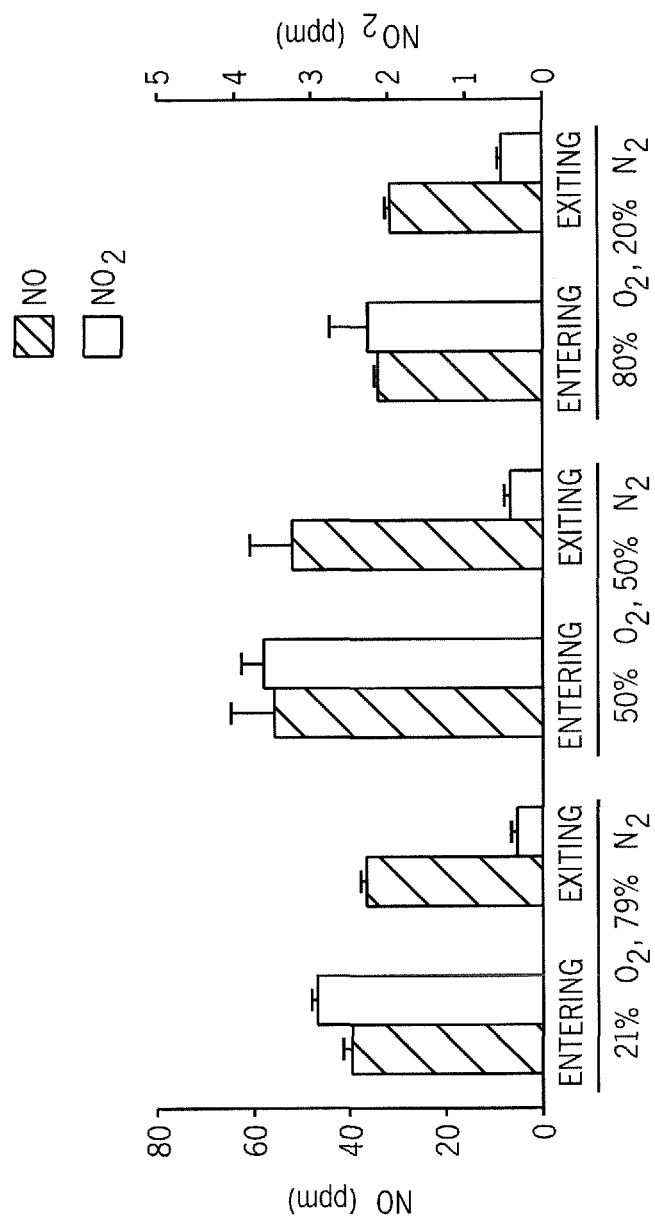
FIG. 16 shows a graph illustrating the NO and $NO_2$ concentrations entering and exiting a scavenger of the nitric oxide generator of FIG. 5.

As described above, the NO generator 102 is similar to the NO generator 14 but is arranged inline on the inspiratory line 18, upstream of exhaled $CO_2$, which enables the scavenger 42 to be of a reduced size. The NO generator 102 was tested at a constant gas flow rate of 5 L/min. The test was performed using the test setup shown in FIG. 10 at atmospheric pressure. The electrodes 36 were fabricated from iridium-platinum. The scavenger 42 comprised 15 g of $Ca(OH)_2$ and the post-filter 44 was placed downstream of the scavenger 42. The controller 33 was configured to spark the electrodes 36 using the following settings: B=35, N=25, P=240 μs; and H=70 μs. The NO and $NO_2$ concentrations generated by the NO generator 102 were measured entering (i.e., upstream) and exiting (i.e., downstream) the scavenger 42 at oxygen levels of 21% (i.e., air), 50%, and 80%, and a balanced amount of nitrogen. FIG. 16 shows the concentrations of NO and $NO_2$ measured during the test. As shown in FIG. 16, the scavenger 42 removed approximately over 95% of the $NO_2$ produced by the NO generator 102. These results are similar to the larger (75 g) scavenger 42. Thus, the smaller scavenger 42 with less gas flow resistance (e.g., 0.2 cmH20*min*$L^{-1}$), used in the NO generator 102, efficiently removes $NO_2$ without reducing the NO concentrations.

Example 7: Measuring and Scavenging $O_3$ Concentrations Produced by the NO Generator 14

Figure 17:
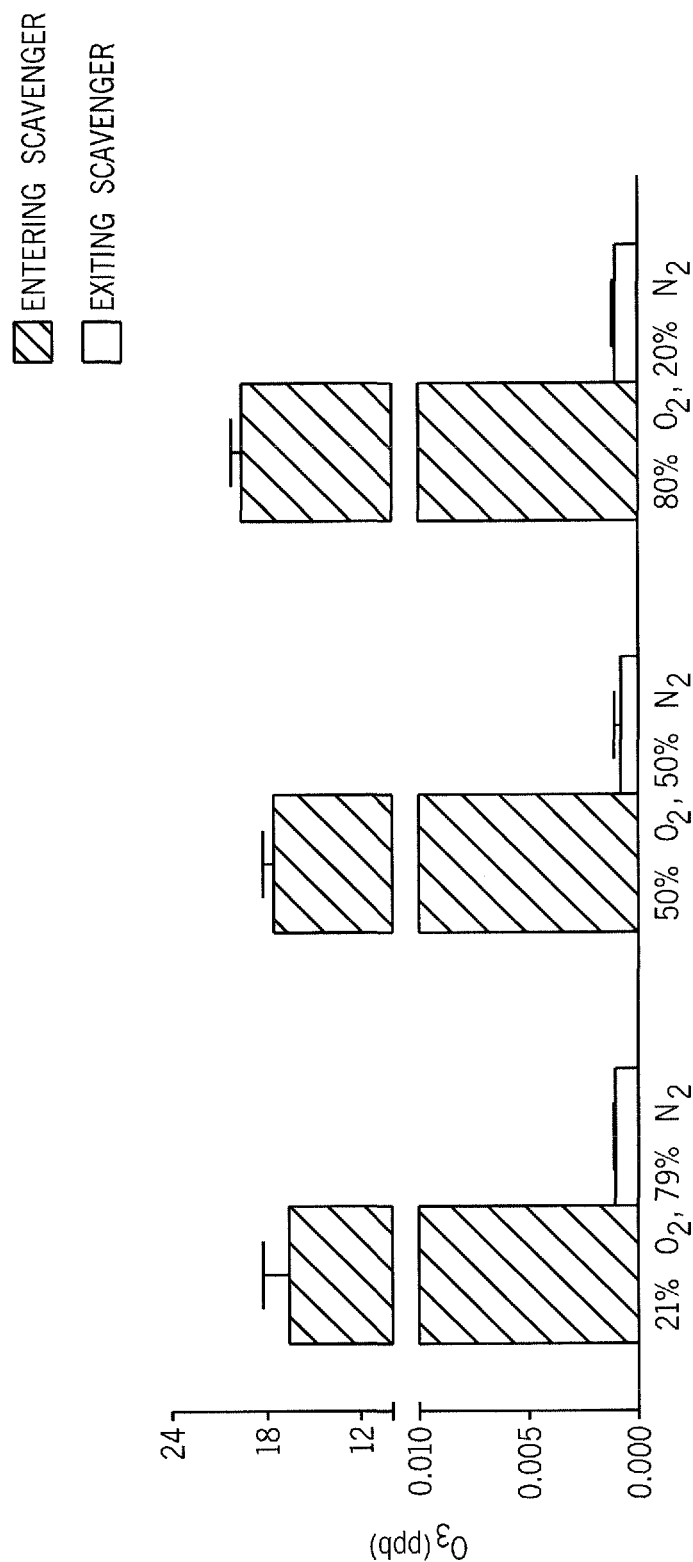
FIG. 17 shows a graph illustrating the ozone ($O_3$) concentrations entering and exiting a scavenger of the nitric oxide generator of FIG. 2.

The NO generator 14 was tested at a constant gas flow rate of 5 L/min. The electrodes 36 were fabricated from iridium-platinum. The test was performed using the test setup shown in FIG. 10 and at atmospheric pressure. The scavenger 42 comprised 72 grams (g) of $Ca(OH)_2$ and the post-filter 44 was placed downstream of the scavenger 42. The controller 33 was configured to spark the electrodes 36 using the following settings: B=25, N=35, P=240 μs; and H=100 μs. The $O_3$ concentrations generated by the NO generator 14 were measured entering (i.e., upstream) and exiting (i.e., downstream) of the scavenger 42 at oxygen levels of 21% (i.e., air), 50%, and 80%, and a balanced amount of nitrogen. FIG. 17 shows the concentrations of $O_3$ measured during the test. As shown in FIG. 17, at 21% oxygen (i.e., in air), the NO generator 14 produced 17±2 parts per billion (ppb) $O_3$ and <0.1 ppb exited the scavenger 42. At 50% oxygen, the NO generator 14 produced 18±10 ppb $O_3$ and <0.1 ppb exited the scavenger 42. At 80% oxygen, the NO generator 14 produced 20±1 ppb $O_3$ and <0.1 ppb exited the scavenger 42. These results demonstrate that the scavenger 42 is highly efficient at removing $O_3$ to negligible levels well below the EPA $O_3$ limits. Similar results were achieved when testing of the smaller scavenger 42 of the NO generator 102.

Example 8: Electrode Erosion

Figure 18B:
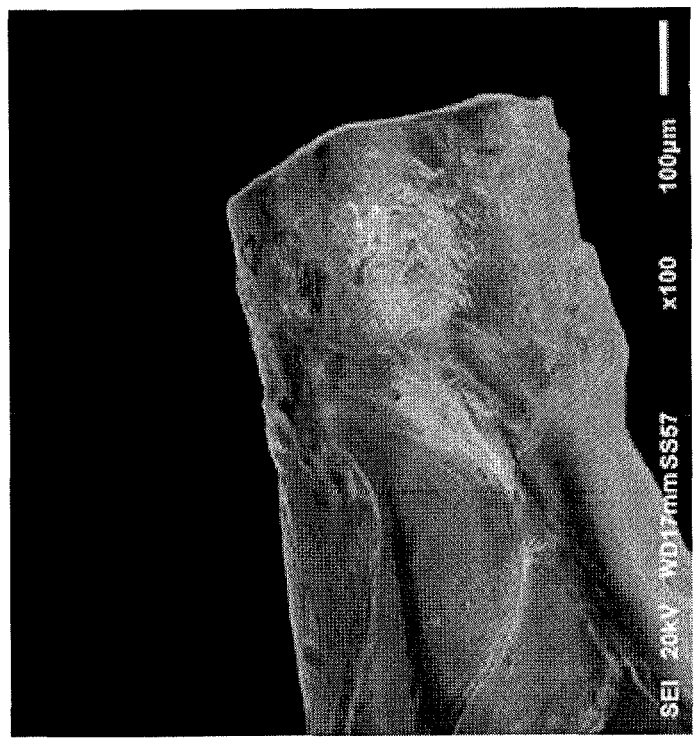
FIG. 18B shows a magnified view of the electrode tip of FIG. 18A after continuous sparking for 10 days.
Figure 18A:
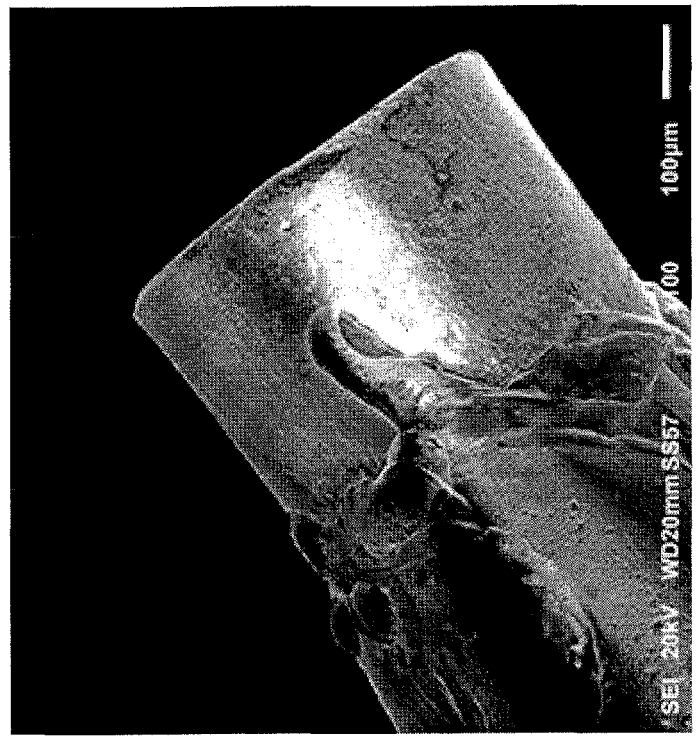
FIG. 18A shows a magnified view of an unused electrode tip.
Figure 19B:
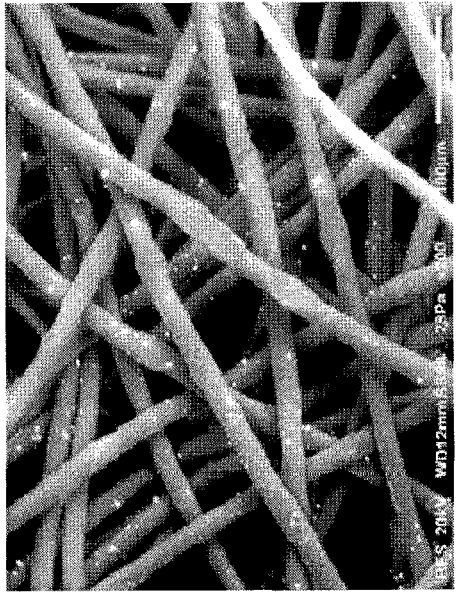
FIG. 19B shows a magnified view of the filter of FIG. 19A after being arranged downstream of electrodes continuously sparking for 10 days.
Figure 20B:
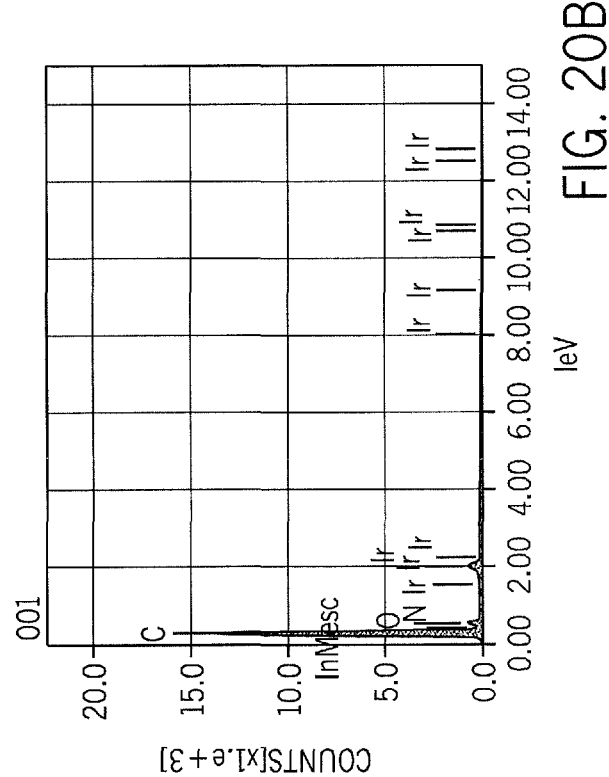
FIG. 20B shows a graph illustrating the energy-dispersive X-ray (EDX) spectroscopy results of the filter of FIG. 19B.
Figure 19A:
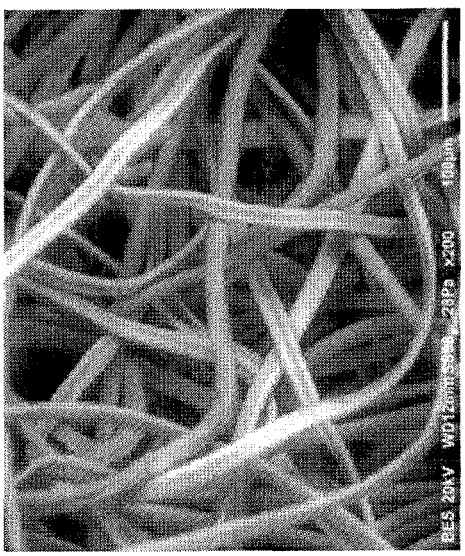
FIG. 19A shows a magnified view of an unused filter.
Figure 20A:
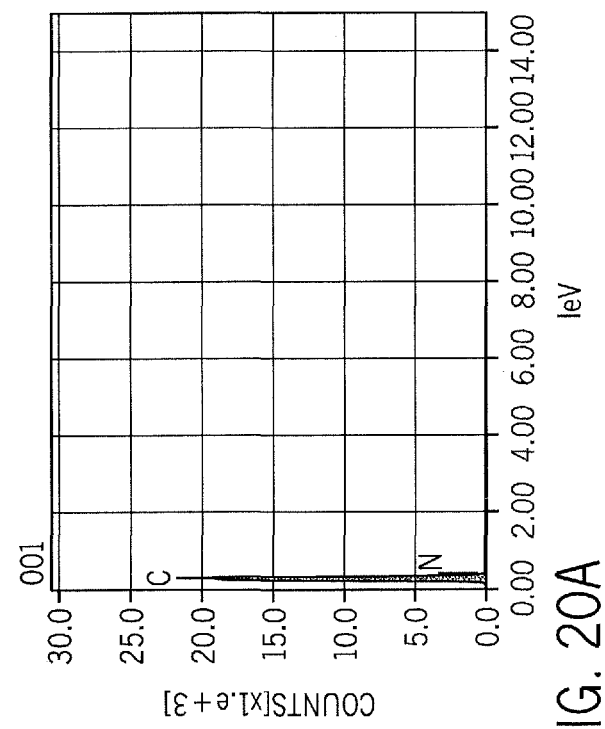
FIG. 20A shows a graph illustrating the energy-dispersive X-ray (EDX) spectroscopy results of the filter of FIG. 19A

As described above, the electrodes can break down and vaporize over time due to the sparking. FIG. 18A shows a new iridium electrode tip and FIG. 18B shows a used iridium electrode tip after ten days of operation producing 50 ppm NO at 5 L/min gas flowrate. As shown in FIG. 18B, the electrode tip has degraded and lost material due to the sparking events. Thus, the requirement for the post-filter 44 in the NO generator 14 and 102, and the post-filter 218 in the NO generator 201 and 301. As the electrodes erode and vaporize, the electrode fragments are deposited on the post-filter 44, 218. To verify that the post-filter 44, 218 catches the electrode fragments, a post-filter with a 0.22 μm particle size cutoff was imaged after the ten days of sparking. FIG. 19A shows a new 0.22 μm post-filter and FIG. 19B shows the 0.22 μm post-filter after the ten days of operation. As shown in FIG. 19B, the used 0.22 μm post-filter contains iridium fragments. This was verified by energy-dispersive X-ray (EDX) spectroscopy as shown in the plots of FIG. 20A and FIG. 20B. FIG. 20A shows the EDX spectroscopy of the new 0.22 μm post-filter and FIG. 20B shows the EDX spectroscopy of the used 0.22 μm post-filter. As shown in FIGS. 20A and 20B, the used 0.22 μm post-filter contains iridium while the new 0.22 μm post-filter does not contain iridium. Thus, a single 0.22 μm post-filter was sufficient and necessary to catch electrode fragments produced by electrode erosion.

Example 9: Minimizing $NO_2$ Generation by Varying Electrode Composition

Figure 21:
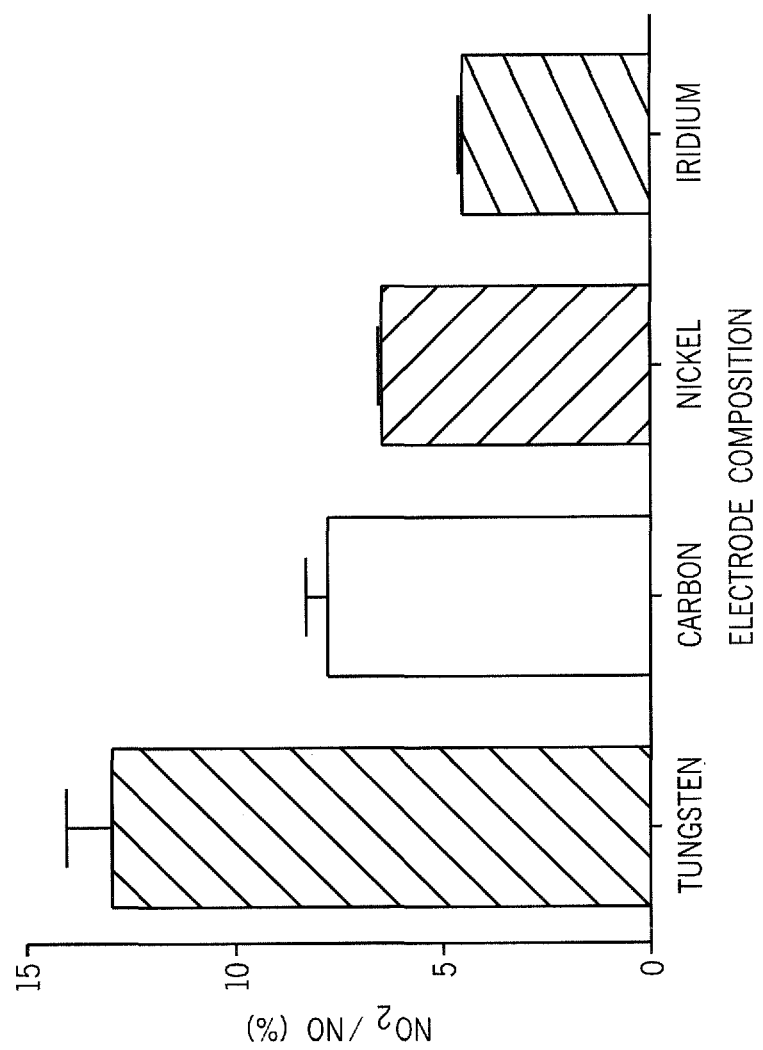
FIG. 21 shows a graph illustrating the $NO_2$/NO ratio generated by electrodes fabricated from various metals.

The NO generator 14 was tested at a constant gas flow rate of 5 L/min with electrodes 36 fabricated from tungsten carbide, carbon, nickel, and iridium. The test was performed using the test setup shown in FIG. 10 and at atmospheric pressure. The controller 33 was configured to spark the electrodes 36 using the following settings: B=25, N=35, P=240 μs; and H=50 μs. FIG. 21 shows the ratio of $NO_2$/NO generated for the different electrode compositions. As shown in FIG. 21, the iridium electrode produced 4.5±0.1% of $NO_2$/NO, the nickel electrode produced 6.5±0.1% of $NO_2$/NO, the carbon electrode produced 7.8±0.5% of $NO_2$/NO, and the tungsten carbide electrode generated 12.9±1.9% of $NO_2$/NO. Obviously, the lower the ratio of $NO_2$/NO the better and, thus, the iridium electrode is an ideal candidate for the composition of the electrodes 36.

Example 10: Measuring NO and $NO_2$ Diffusion Rates Through the Membrane 104 of the NO Generator 102

Figure 22:
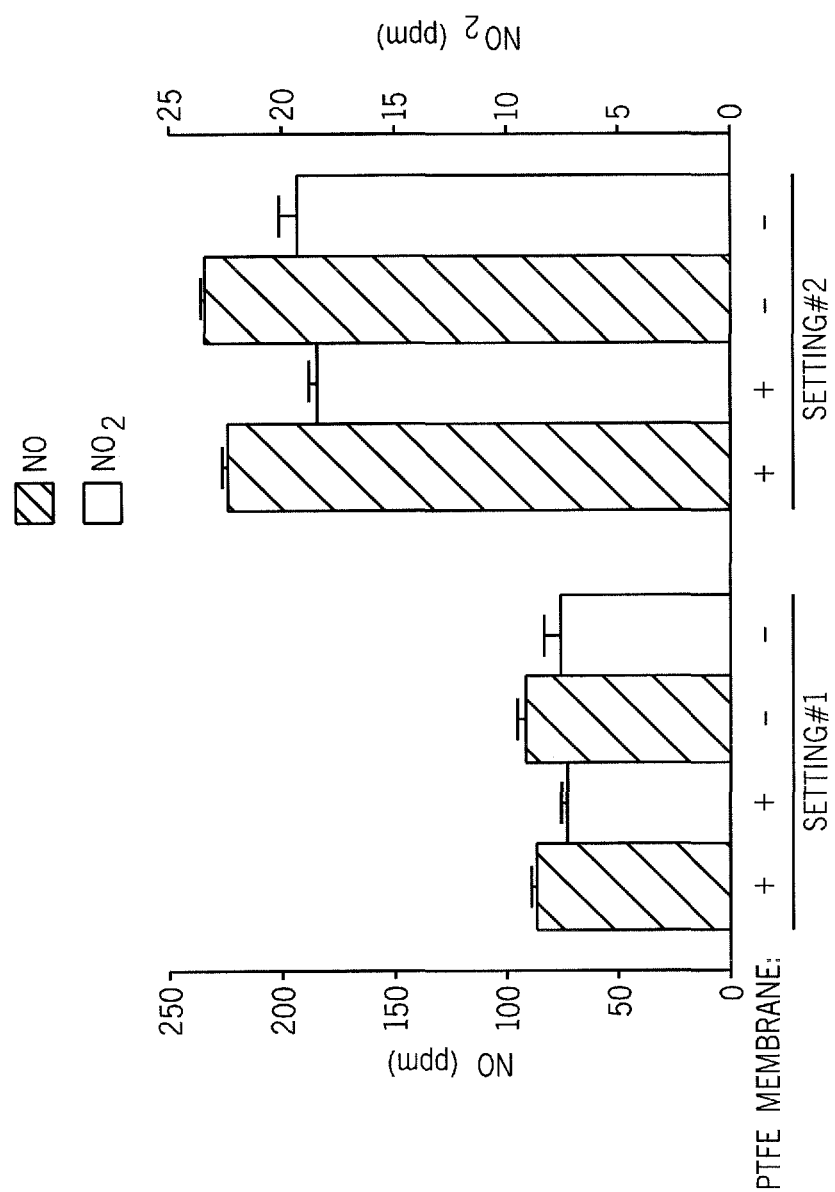
FIG. 22 shows a graph illustrating the NO and $NO_2$ concentrations generated with and without a microporous membrane covering the nitric oxide generator of FIG. 5.

As described above, since the NO generator 102 is placed inline with the inspiratory line 18, the microporous membrane 104 can be placed around the electrodes 36 to protect them from droplets of water or airway secretions. The NO generator 102 was tested at a constant gas flow rate of 0.5 L/min for 5 minutes while producing NO. The NO and $NO_2$ produced was averaged over the 5 minutes and the concentrations with (+) and without (−) the membrane 104 were measured. The controller 33 was configured to spark the electrodes 36 using the following two sets of settings. Setting #1: B=25, N=35, P=240 μs; and H=30 μs. Setting #2: B=25, N=35, P=240 μs; and H=60 μs. FIG. 22 shows the NO and $NO_2$ concentrations produced during the 5 minutes with (+) and without (−) the membrane 104 at the two different spark settings. As shown in FIG. 22, 95±2% of the NO generated without (−) the membrane 104 was generated with (+) the membrane 104, and 95±1% of the $NO_2$ generated without (−) the membrane 104 was generated with (+) the membrane 104. Thus, the addition of the membrane 104 does not significantly alter the NO production characteristics of the NO generator 102.

Animal Studies

Animal studies were approved by the Institutional Animal Care and Use Committee of Massachusetts General Hospital (Boston, Mass.). Eight lambs (New England Ovis, Dover, N.H.) weighing 32±2 kg were studied. General anesthesia was induced with 5% inhaled isoflurane (1-chloro-2,2,2-trifluoroethyldifluromethyl ether, Baxter, Deerfield, Ill.) in oxygen delivered via a mask and then maintained with 1-4% isoflurane in 50% oxygen during surgery. After tracheal intubation, the lambs were instrumented with indwelling carotid artery pulmonary artery catheters. All hemodynamic measurements were performed in anesthetized lambs ventilated with a mechanical ventilator (model 7200, Puritan Bennett, Pleasanton, Calif.) at a tidal volume of 400 ml/min and rate of 1245 breaths/min.

To induce pulmonary hypertension, a potent pulmonary vasoconstrictor U46619 (Cayman Chemical, Ann Arbor, Mich.), the analog of the endoperoxide prostaglandin 112, was infused intravenously at a rate of 0.8-0.9 µg/kg/min to increase pulmonary arterial pressure (PAP) to 30 mmHg. The mean arterial pressure and PAP were continuously monitored using a Gould 6600 amplifier system (Gould Electronics, Inc., Eastlake, Ohio). Pulmonary capillary wedge pressure, heart rate, and cardiac output were intermittently measured at baseline, during U46619 infusion, and before and after inhalation of NO generated using either the respiratory system 10, the respiratory system 100, or NO delivered and diluted at the same level from a compressed gas cylinder. Cardiac output was assessed by thermal dilution as the average of three measurements after an intravenous bolus injection of 10 mL of ice-cold saline solution. Pulmonary vascular resistance index (PVRI), as well as cardiac index (CI), were calculated using standard formulae. The gas cylinder contained 500 ppm NO diluted in nitrogen.

Example 11: Continuous NO Generation from Air Using the Respiratory System 10 on Anesthetized Lambs The respiratory system 10 was tested with an anesthetized lamb as the patient 11. A baseline (BL) was generated then the NO generator 14 of the respiratory system 10 was triggered to continuously spark (i.e., generate NO) after U46619 was administered for 30 minutes. The NO was pumped at 5 L/min into the inspiratory line 18. The electrodes 36 were fabricated from iridium-platinum. Once triggered, the controller 33 was configured to spark the electrodes 36 for 4 minutes using the following settings: B=35, N=25, P=240 µs; and H=100 µs, which produced approximately 40 ppm of NO, and then the controller 33 stopped the NO generator 14. The test was performed when 21% oxygen was supplied to the inlet 24 of the NO generator 14, when 50% oxygen was supplied to the inlet 24 of the NO generator 14, and compared with NO supplied at the same concentration to the anesthetized lamb from a gas cylinder.

Figure 23A:
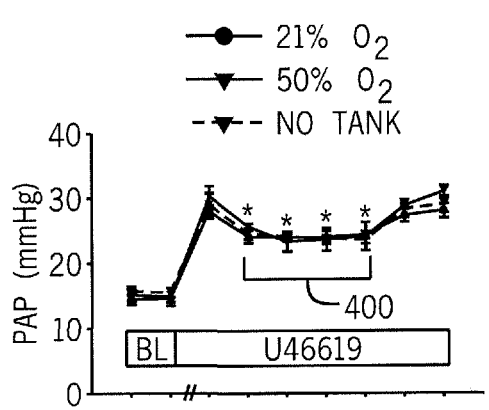
FIG. 23A shows a graph illustrating the mean pulmonary artery pressure (PAP) of an anesthetized lamb with acute pulmonary hypertension due to U46619 infusion following inhalation of nitric oxide generated using the respiratory system of FIG. 1 and compared with nitric oxide delivered from a compressed $NO/N_2$ gas cylinder.
Figure 23B:
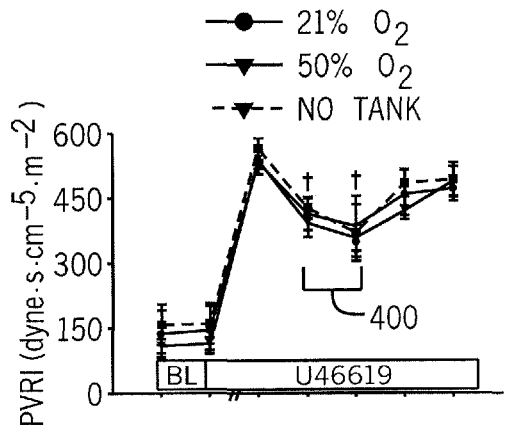
FIG. 23B shows a graph illustrating the pulmonary vascular resistance index (PVRI) of an anesthetized lamb with acute pulmonary hypertension following inhalation of nitric oxide generated using the respiratory system of FIG. 1 and compared with nitric oxide delivered from a compressed $NO/N_2$ gas cylinder.

FIG. 23A shows the mean pulmonary artery pressure (PAP) of the anesthetized lamb for the duration of the tests, and FIG. 23B shows the pulmonary vascular resistance index (PVRI) of the anesthetized lamb for the duration of the tests. As shown in FIGS. 23A and 23B, during the 4 minute window 400 when NO was continuously produced by the NO generator 14, PAP and PVRI were rapidly reduced while breathing both 21% and 50% oxygen. Also, the reduction in PAP and PVRI for the NO produced by the NO generator 14 was similar to the reduction in PAP and PVRI for the NO supplied at the same level by dilution from the gas cylinder. Therefore, the respiratory system 10 can be a viable and equivalent replacement for gas cylinders when administering NO inhalation therapy.

Example 12: Continuous NO Generation from Air Using the Respiratory System 100 on Anesthetized Lambs The respiratory system 100 was tested with an anesthetized lamb as the patient 11. A baseline (BL) was generated then the NO generator 102 of the respiratory system 100 was triggered to continuously spark (i.e., generate NO) after U46619 was administered for 30 minutes. The electrodes 36 were fabricated from iridium-platinum. Once triggered, the controller 33 was configured to spark the electrodes 36 for 4 minutes using the following settings: B=35, N=25, P=240 µs; and H=100 µs, which produced approximately 40 ppm of NO, and then the controller 33 stopped the NO generator 102. The test was performed when 21% oxygen was supplied in the inspiratory line 18, when 50% oxygen was supplied in the inspiratory line 18, and when NO was supplied to the anesthetized lamb diluted from a compressed gas cylinder.

Figure 24A:
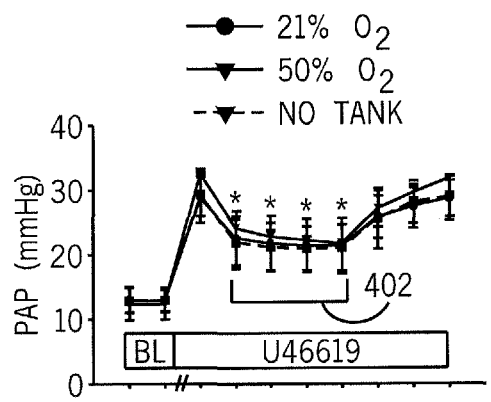
FIG. 24A shows a graph illustrating the mean pulmonary artery pressure (PAP) of an anesthetized lamb with acute pulmonary hypertension following inhalation of nitric oxide generated using the respiratory system of FIG. 4 with the nirtic oxide generator continuously sparking and compared with nitric oxide delivered from a compressed gas cylinder.
Figure 24B:
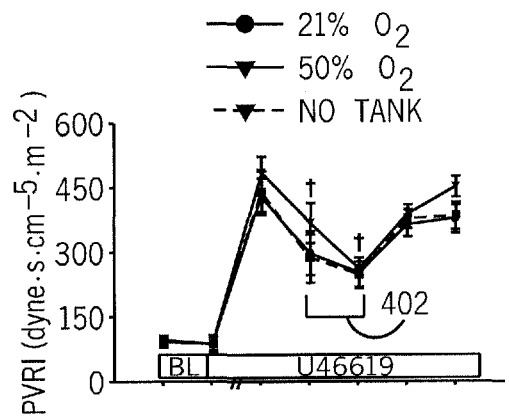
FIG. 24B shows a graph illustrating the pulmonary vascular resistance index (PVRI) of an anesthetized lamb with acute pulmonary hypertension following inhalation of nitric oxide generated using the respiratory system of FIG. 4 with the nitric oxide generator continuously sparking and compared with nitric oxide delivered from a compressed gas cylinder.

FIG. 24A shows the mean pulmonary artery pressure (PAP) of the anesthetized lamb for the duration of the tests, and FIG. 24B shows the pulmonary vascular resistance index (PVRI) of the anesthetized lamb for the duration of the tests. As shown in FIGS. 24A and 24B, during the 4 minute window 402 when NO was continuously produced by the NO generator 102, PAP and PVRI were rapidly reduced while breathing both 21% and 50% oxygen. Also, the reduction in PAP and PVRI for the NO produced by the NO generator 102 was similar to the reduction in PAP and PVRI for the NO supplied by the gas cylinder. Also, the performance of the respiratory system 100 was similar to the respiratory system 10. Therefore, the respiratory system 100 can provide a viable and equivalent replacement for compressed gas cylinders when administering NO inhalation therapy.

Example 13: Intermittent NO Generation from Air Using the Respiratory System 100 on Anesthetized Lambs The respiratory system 100 was tested with an anesthetized lamb as the patient 11. A baseline (BL) was generated then the NO generator 102 of the respiratory system 100 was triggered to intermittently spark (i.e., generate NO) after U46619 was administered for 30 minutes. The electrodes 36 were fabricated from iridium-platinum. The controller 33 was configured to spark the electrodes 36 only during the first 0.8 seconds of inspiration for 4 minutes using the following settings: B=35, N=25, P=240 µs; and H=100 µs and then the controller 33 stopped the NO generator 102. The test was performed when 21% oxygen was supplied in the inspiratory line 18, when 50% oxygen was supplied in the inspiratory line 18, and when NO was supplied to the anesthetized lamb from a gas cylinder.

Figure 25A:
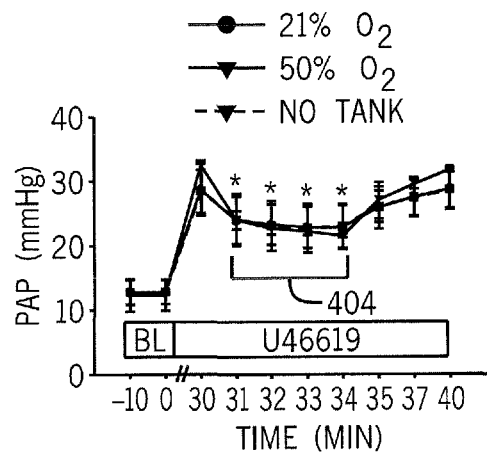
FIG. 25A shows a graph illustrating the mean pulmonary artery pressure (PAP) of an anesthetized lamb with acute pulmonary hypertension following inhalation of nitric oxide generated using the respiratory system of FIG. 4 with the nitric oxide generator intermittenly sparking and compared with nitric oxide delivered from a compressed gas cylinder.
Figure 25B:
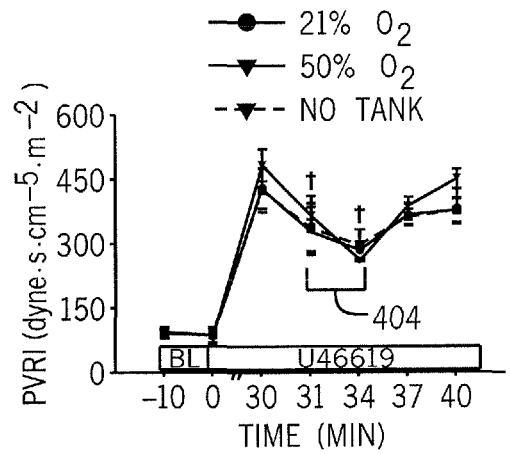
FIG. 25B shows a graph illustrating the pulmonary vascular resistance index (PVRI) of an anesthetized lamb with acute pulmonary hypertension following inhalation of nitric oxide generated using the respiratory system of FIG. 2 with the nitric oxide generator intermittently sparking and compared with nitric oxide delivered from a compressed gas cylinder.

FIG. 25A shows the PAP of the anesthetized lamb for the duration of the tests, and FIG. 25B shows the PVRI of the anesthetized lamb for the duration of the tests. As shown in FIGS. 24A and 24B, during the 4 minute window 404 when NO was produced during the first 0.8 seconds of inspiration by the NO generator 102, mean pulmonary artery pressure (PAP) and the pulmonary vascular resistance index (PVRI) were rapidly reduced breathing either 21% and 50% oxygen. Also, the reduction in PAP and PVRI for the NO produced by the NO generator 102 was similar to the reduction in PAP and PVRI for NO supplied and diluted from the compressed gas cylinder. Also, the performance of the respiratory system 100 when intermittently sparking the electrodes 36 was similar to the respiratory system 100 and the respiratory system 10 when continuously sparking the electrodes 36. Therefore, intermittently generating NO with the respiratory system 100 can be a viable replacement for gas cylinders when administering NO inhalation therapy.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments. Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

While the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. An apparatus for generating nitric oxide comprising: two or more electrodes;
a scavenger arranged downstream of the electrodes to filter at least nitrogen dioxide ($NO_2$);
one or more sensors configured to measure at least one of a flowrate of gas, an oxygen concentration upstream of the electrodes, a nitric oxide concentration downstream of the electrodes, and a nitrogen dioxide concentration downstream of the electrodes;
a controller in communication with the electrodes and the one or more sensors and configured to supply an electrical signal to the electrodes that controls timing and sparking characteristics of the electrodes such that the timing and the sparking characteristics of the electrodes determine a concentration of nitric oxide generated by the electrodes,
the controller being configured to monitor a condition of the scavenger by determining if the concentration of nitrogen dioxide as measured by the one or more sensors exceeds a predetermined value such that the controller is configured to one or more of instruct a user to replace the scavenger and cease supplying the electric signal to the electrodes to cease nitric oxide production.

2. The apparatus of claim 1, wherein the electrodes comprise at least one of tungsten carbide, carbon, nickel, iridium, titanium, rhenium, and platinum.

3. The apparatus of claim 1, wherein the electrodes comprise iridium.

4. The apparatus of claim 1, wherein the scavenger is fabricated from calcium hydroxide.

5. The apparatus of claim 1, wherein the one or more sensors include an airway flowmeter arranged downstream of the electrodes, an oxygen sensor arranged upstream of the electrodes, a nitric oxide sensor arranged downstream of the electrodes, and a nitrogen dioxide sensor arranged downstream of the electrodes.

6. The apparatus of claim 1, wherein an ignition coil is in communication with the controller and the electrodes.

7. The apparatus of claim 6, wherein the controller is further configured to instruct the ignition coil to supply stored electrical energy to the electrodes.

8. The apparatus of claim 1, wherein the electrical signal supplied to the electrodes controls at least one of a number of electrode spark groups per second, a number of individual electrode sparks per spark group, a time between individual electrode sparks, and a pulse duration.

9. The apparatus of claim 8, wherein the controller is further configured to vary at least one of the number of electrode spark groups per second, the number of individual electrode sparks per spark group, the time between individual electrode sparks, and the pulse duration in response to feedback from the one or more sensors.

10. The apparatus of claim 1, further comprising a gas pump arranged upstream of the electrodes.

11. The apparatus of claim 1, wherein the one or more sensors provide an indication of inspiration.

12. The apparatus of claim 11, wherein the controller is further configured to supply the electrical signal to the electrodes in response to detecting inspiration.

13. The apparatus of claim 1, wherein a filter arranged downstream of the electrodes is configured to filter particles flowing downstream of the electrodes with a diameter greater than approximately 0.22 micrometers.

14. The apparatus of claim 1, wherein the one or more sensors are configured to further measure at least one of a pressure of the gas flowing to the electrodes, temperature of the gas flowing to the electrodes, and humidity of the gas flowing to the electrodes.

15. An apparatus for generating nitric oxide to be integrated into a respiratory system having a breathing apparatus, an inspiratory line, and an airway flowmeter associated with the inspiratory line, the apparatus comprising:
two or more electrodes in communication with the inspiratory line;
a scavenger arranged downstream of the electrodes to filter at least nitrogen dioxide ($NO_2$);
one or more sensors configured to measure at least one of an oxygen concentration upstream of the electrodes, a barometric pressure, a nitric oxide concentration downstream of the electrodes, and a nitrogen dioxide concentration downstream of the electrodes;
a controller in communication with the electrodes, the one or more sensors, and the airway flowmeter, and configured to supply an electrical signal to the electrodes that controls timing and sparking characteristics of the electrodes such that the timing and the sparking characteristics of the electrodes determine a concentration of nitric oxide generated by the electrodes,
the controller being configured to monitor a condition of the scavenger by determining if the concentration of nitrogen dioxide as measured by the one or more sensors exceeds a predetermined value such that the controller is configured to one or more of instruct a user to replace the scavenger.

16. The apparatus of claim 15, wherein the electrodes are arranged between an inlet and an outlet, the outlet coupled to the inspiratory line.

17. The apparatus of claim 16, further comprising a gas pump arranged upstream of the electrodes.

18. The apparatus of claim 15, wherein the electrodes are at least partially integrated into the inspiratory line.

19. The apparatus of claim 18, wherein a filter is arranged in the inspiratory line.

20. The apparatus of claim 18, wherein the scavenger is arranged in the inspiratory line.

21. The apparatus of claim 18, wherein the airway flowmeter provides an indication of inspiration.

22. The apparatus of claim 21, wherein the controller is further configured to supply the electrical signal to the electrodes in response to detecting inspiration.

23. The apparatus of claim 15, wherein the electrodes comprise at least one of tungsten carbide, carbon, nickel, iridium, titanium, rhenium, and platinum.

24. The apparatus of claim 15, wherein the electrodes comprise iridium.

25. The apparatus of claim 15, wherein the scavenger is fabricated from calcium hydroxide.

26. The apparatus of claim 15, wherein the one or more sensors include an oxygen sensor arranged upstream of the electrodes, a nitric oxide sensor arranged downstream of the electrodes, and a nitrogen dioxide sensor arranged downstream of the electrodes.

27. The apparatus of claim 15, wherein an ignition coil is in communication with the controller and the electrodes.

28. The apparatus of claim 27, wherein the controller is further configured to instruct the ignition coil to supply stored electrical energy to the electrodes.

29. The apparatus of claim 15, wherein the electrical signal supplied to the electrodes controls at least one of a number of electrode spark groups per second, a number of individual electrode sparks per spark group, a time between individual electrode sparks, and a pulse duration.

30. The apparatus of claim 29, wherein the controller is further configured to vary at least one of the number of electrode spark groups per second, the number of individual electrode sparks per spark group, the time between individual electrode sparks, and the pulse duration in response to feedback from the one or more sensors.

31. The apparatus of claim 15, wherein a filter arranged downstream of the electrodes is configured to filter particles flowing downstream of the electrodes with a diameter greater than approximately 0.22 micrometers.

32. The apparatus of claim 15, wherein the breathing apparatus comprises one of a ventilator system, a continuous positive airway pressure (CPAP) system, a High Frequency Oscillatory Ventilator (HFOV), a face mask, a nasal cannula or an inhaler.

33. An apparatus for generating nitric oxide to be integrated into a respiratory system having a breathing apparatus and an inspiratory line, the apparatus comprising:
a chamber including a chamber inlet and two or more electrodes arranged within the chamber;
a main chamber configured to provide a fluid path to an airway of a patient;
a scavenger arranged downstream of the electrodes to filter at least nitrogen dioxide ($NO_2$);
one or more sensors configured to measure at least one of an oxygen concentration upstream of the electrodes, a barometric pressure, a nitric oxide concentration downstream of the electrodes, and a nitrogen dioxide concentration downstream of the electrodes;
a controller in communication with the electrodes and the one or more sensors, and configured to supply an electrical signal to the electrodes that controls sparking characteristics of the electrodes such that the timing and the sparking characteristics of the electrodes determine a concentration of nitric oxide generated by the electrodes,
the controller being configured to monitor a condition of the scavenger by determining if the concentration of nitrogen dioxide as measured by the one or more sensors exceeds a predetermined value such that the controller is configured to one or more of instruct a user to replace the scavenger and cease supplying the electric signal to the electrodes to cease nitric oxide production, and
wherein the chamber is in communication with the main chamber and gas in the chamber is non-mechanically induced into the main chamber.

34. The apparatus of claim 33, wherein the main chamber includes a venturi.

35. The apparatus of claim 34, further comprising a passage connecting the chamber to the venturi of the main chamber.

36. The apparatus of claim 34, wherein a flow of gas through the venturi is configured to draw a vacuum on the chamber.

37. The apparatus of claim 33, further comprising a pre-scavenger arranged upstream of the chamber inlet.

38. The apparatus of claim 33, further comprising a pre-filter arranged upstream of the chamber inlet.

39. The apparatus of claim 33, wherein the main chamber and the chamber define a parallel path.

40. A method of generating nitric oxide in a respiratory system having a breathing apparatus in communication with an airway of a patient, the method comprising:
coupling a nitric oxide generator including a pair of electrodes to the airway of the patient;
triggering the nitric oxide generator to produce a desired concentration of nitric oxide gas;
determining desired sparking characteristics of the electrodes to produce the desired concentration of nitric oxide gas;
once the sparking characteristics have been determined, supplying an electrical signal to the electrodes that initiates the desired sparking characteristics between the electrodes to generate the desired concentration of nitric oxide gas in a flow of gas provided to the airway of the patient;
scavenging at least one of nitrogen dioxide and ozone in the flow of gas provided to the patient using a scavenger; and
monitoring a condition of the scavenger by determining if the concentration of nitrogen dioxide as measured by one or more sensors exceeds a predetermined value such that the controller is configured to one or more of instruct a user to replace the scavenger and cease supplying the electric signal to the electrodes to cease nitric oxide production.

41. The method of claim 40, wherein the breathing apparatus one of a ventilator system, a continuous positive airway system (CPAP) system, a High Frequency Oscillatory Ventilator (HFOV), a face mask, a nasal cannula or an inhaler.

42. The method of claim 40, wherein triggering the nitric oxide generator to produce a desired concentration of nitric oxide gas comprises:
monitoring at least one of a gas flowrate provided to the patient, a temperature of gas provided to the patient, and a pressure of gas provided to the patient;
detecting a change in at least one of the gas flowrate provided to the patient, the temperature of gas provided to the patient, and the pressure of gas provided to the patient; and
determining that the change detected is indicative of an inspiratory event.

43. The method of claim 40, wherein determining desired sparking characteristics of the electrodes comprises:
   measuring an atmospheric pressure; and
   determining a number of electrode spark groups per second, a number of individual electrode sparks per spark group, a time between individual electrode sparks, and a pulse duration.

44. The method of claim 40 further comprising:
   monitoring at least one of a nitric oxide concentration downstream of the electrodes and a nitrogen dioxide concentration downstream of the electrodes;
   determining that at least one of the nitric oxide concentration and the nitrogen dioxide concentration is not equal to a desired concentration; and
   in response to determining that the nitric oxide concentration downstream of the electrodes is not equal to the desired concentration, varying, via the electrical signal, at least one of a number of electrode spark groups per second, a number of individual electrode sparks per spark group, a time between individual electrode sparks, and a pulse duration.

45. The method of claim 40 further comprising:
   monitoring a nitrogen dioxide concentration downstream of the electrodes;
   determining that the nitrogen dioxide concentration is greater than a pre-defined maximum concentration; and
   upon determining that the nitrogen dioxide concentration downstream of the electrodes is greater than the pre-defined maximum concentration, ceasing the supplying of the electrical signal to the electrodes.

* * * * *

UNITED STATES PATENT AND TRADEMARK OFFICE
CERTIFICATE OF CORRECTION

PATENT NO. : 11,497,878 B2
APPLICATION NO. : 15/520137
DATED : November 15, 2022
INVENTOR(S) : Warren Zapol et al.

It is certified that error appears in the above-identified patent and that said Letters Patent is hereby corrected as shown below:

In the Specification

Column 5, Lines 66-67, "concentrationthe" should be --concentration for the--.

Column 6, Line 55, "nirtic" should be --nitric--.

Column 7, Line 1, "intermittenly" should be --intermittently--.

Column 16, Line 27, "FIG. 13" should be --FIG. 14--.

Column 19, Line 12, "1245" should be --12-15--.

Column 19, Line 15, "112" should be --$H_2$--.

Signed and Sealed this
Fourteenth Day of March, 2023

Katherine Kelly Vidal
*Director of the United States Patent and Trademark Office*